United States Patent
Kumar et al.

(10) Patent No.: US 10,196,459 B2
(45) Date of Patent: Feb. 5, 2019

(54) INTRINSICALLY DISORDERED PROTEIN BRUSHES

(71) Applicant: The Regents of the University of California, Oakland, CA (US)

(72) Inventors: Sanjay Kumar, Moraga, CA (US);
Nithya Srinivasan, Berkeley, CA (US);
Maniraj Bhagawati, Hannover (DE);
Badriprasad Ananthanarayanan, Albany, CA (US)

(73) Assignee: The Regents of the University of California, Oakland, CA (US)

(*) Notice: Subject to any disclaimer, the term of this patent is extended or adjusted under 35 U.S.C. 154(b) by 208 days.

(21) Appl. No.: 15/143,557

(22) Filed: Apr. 30, 2016

(65) Prior Publication Data

US 2016/0319041 A1 Nov. 3, 2016

Related U.S. Application Data

(60) Provisional application No. 62/155,397, filed on Apr. 30, 2015.

(51) Int. Cl.
| | | |
|---|---|---|
| A61L 27/34 | (2006.01) | |
| A61L 29/08 | (2006.01) | |
| A61L 31/10 | (2006.01) | |
| C07K 17/14 | (2006.01) | |

(52) U.S. Cl.
CPC .............. *C07K 17/14* (2013.01); *A61L 27/34* (2013.01); *A61L 29/085* (2013.01); *A61L 31/10* (2013.01); *A61L 2420/00* (2013.01)

(58) Field of Classification Search
None
See application file for complete search history.

(56) References Cited

PUBLICATIONS

Sellner et al., "Hyperacute Detection of Neurofilament Heavy Chain in Serum Following Stroke: A Transient Sign", Neurochem Res. 36: 2287-2291 (2011).*

* cited by examiner

*Primary Examiner* — Anand U Desai
(74) *Attorney, Agent, or Firm* — Gavrilovich, Dodd & Lindsey LLP

(57) ABSTRACT

The disclosure relates to molecular protein brushes and devices comprising regions of protein brushes.

14 Claims, 18 Drawing Sheets
Specification includes a Sequence Listing.

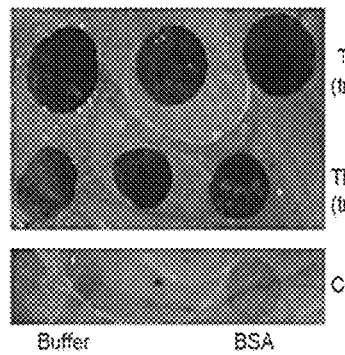
FIG. 14B
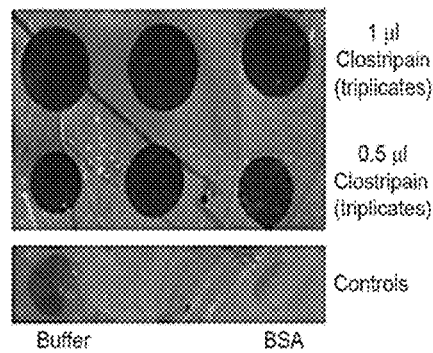
FIG. 14C
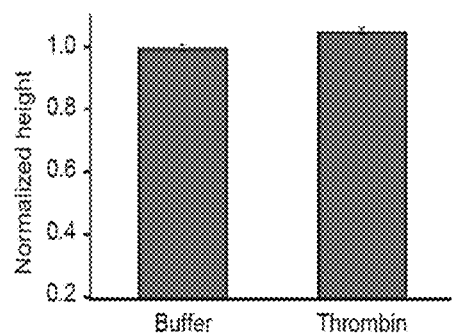
FIG. 14D
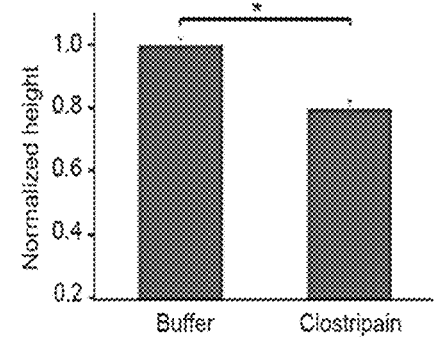
FIG. 14E
| Name | Sequence | Nominal pI | Charge at respective pH | | |
|------|----------|------------|---|---|---|
| | | | 5 | 7.5 | 10 |
| KSP | CEAKSPVKEEAKSPAEAKSPEKEEAKSPAEVK | 5.3 | 0.6 | -1.4 | -7.2 |
| KDP | CEAKDPVKEEAKDPAEAKDPEKEEAKDPAEVK | 4.5 | -2.6 | -5.4 | -11.2 |
FIG. 15A

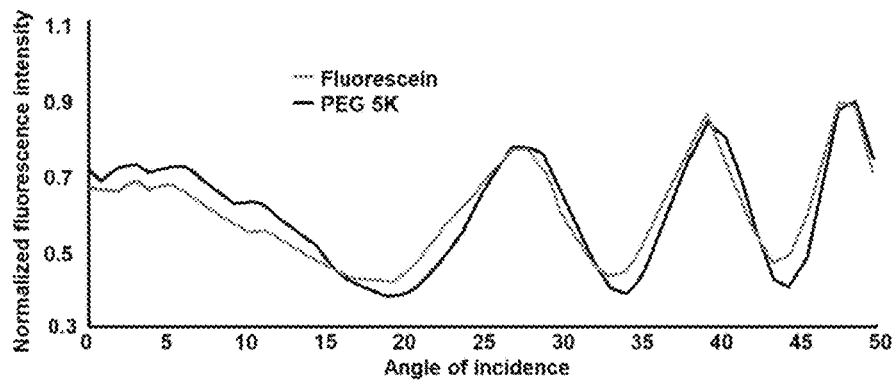
FIG. 20A
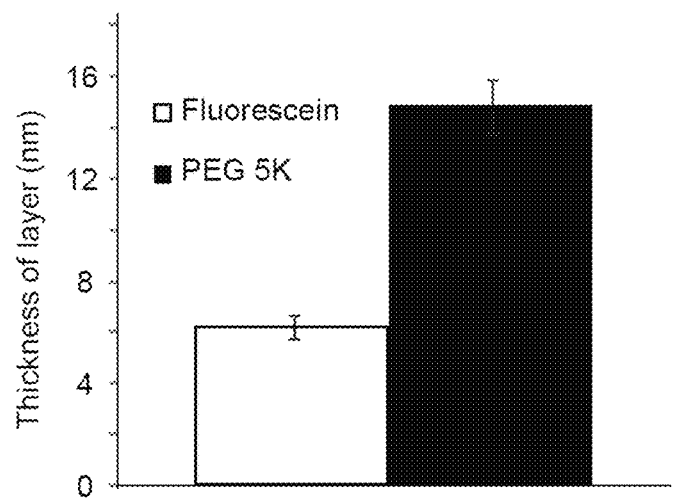
FIG. 20B
Fluorescein-KVEAPSKAEEKEPSKAEAPSKAEEKVPSKAEC
Fluorescein-KVEAPDKAEEKEPDKAEAPDKAEEKVPDKAEC
*FIG. 21*

INTRINSICALLY DISORDERED PROTEIN BRUSHES

CROSS REFERENCE TO RELATED APPLICATIONS

This application claims priority to U.S. Provisional Application Ser. No. 62/155,397 filed Apr. 30, 2015, the disclosure of which is incorporated herein by reference.

TECHNICAL FIELD

The disclosure relates to molecular protein brushes and devices comprising regions of protein brushes.

BACKGROUND

Polymer brushes form when macromolecular chains are end-tethered to surfaces at high grafting densities. The swelling and mutual steric repulsion of the polymers cause the chains to stretch and extend into the solvent, producing a molecular coating that can reduce non-specific interactions of the underlying surface with cells and biological macromolecules. However, because these brushes are almost universally constructed from synthetic polymers, they are frequently somewhat heterogeneous and are challenging to modify at specific monomeric positions along the chain.

SUMMARY

The disclosure provides a protein-based polymer brush system whose conformational properties can be strongly modulated by changes in pH and ionic strength. In addition, the dynamic range can be shifted, widened, or narrowed in interesting ways by exerting more control over the grafting density. Furthermore, proteases can be used to reduce the height of the brush in situ by cleaving the constituent chains at well-defined points.

The disclosure provides a protein brush comprising: (a) a substrate and (b) a plurality of polypeptides, each polypeptide having a first end and second end, wherein the first end is linked to the substrate, wherein the polypeptides comprise a sequence of amino acids selected so as to not form secondary structures; wherein the polypeptides change conformation with the ionic and/or pH of the environment. In one embodiment, the polypeptide is linked to the substrate with an anchoring group selected from the group consisting of hydroxyl group, a thiol group, an azide group, a carboxylic acid group, an amide group, an amine group, an epoxide group, a vinyl group, and a trichlorosilane group. In another embodiment, the polypeptide contains a large and substantially equal number of cationic and anionic amino acids. In yet another embodiment of any of the foregoing the polypeptide comprises phosphorylatable amino acids that can be phosphorylated or de-phosphorylated to modulate the charge on the amino acid. In still another embodiment of any of the foregoing the polypeptide comprises a sequence that is at least 90-100% identical to SEQ ID NO:1 or SEQ ID NO:2. In further embodiment, the polypeptide comprises a fusion polypeptide comprising a sequence 90-100% identical to SEQ ID NO:1 or 2 and at least one additional domain selected from the group consisting of (a) a protease cleavage site, (b) a purification domain, (c) a spacer sequence, (d) a further domain having a sequence 90-100% identical to SEQ ID NO:1 or 2 separated by (a), (b) and/or (c), and any combination of the foregoing.

The disclosure also provides a device comprising protein brush regions. In one embodiment, the protein brush is a medical device.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

FIG. 14A-E shows in situ protease digestion of rNFH-SA brush. (a) Schematic representation of the protease digestion experiment. Digestion is accomplished in situ on immobilized rNFH-SA brush. The thrombin cleavage site (cross) is very close to the surface (19 amino acids deep) while the deepest clostripain digestion site (cross) is 253 amino acids from the top edge of the brush. Although both enzymes cleave off the HN tag leading to a loss of immunofluorescence, only clostripain digestion produces a measurable change in the brush height. Fluorescence image of the protein brushes digested with (b) thrombin and (c) clostripain. The clostripain buffer contains $Ca^{2+}$, a divalent cation that could interact with the HN tag53-55; these interactions likely affect the accessibility of the HN-tag to the antibody, thereby causing a minor decrease in fluorescence. Comparison of normalized brush heights calculated from AFM experiments for (d) thrombin- and (e) clostripain-digested surfaces. Data represent mean±sem. across B 1,000 force curves on a single surface; *P<0.01 by Student's t-test. The brush heights were normalized to the height measured for the corresponding buffer incubated surface (57±4 nm).

FIG. 15A-C shows (A) Details of the peptides used in this study (SEQ ID NOs: 3 and 4). (B) Kratky plots derived from small angle X-ray scattering (SAXS) of the two peptides dissolved in buffer of ionic strength 150 mM, pH 7.5. (C) Radii of gyration (Rg) of the peptides calculated using ensemble optimized modeling of the SAXS spectra of the peptides in buffers of varying ionic strength at pH 7.5. The error bars represent standard deviations of radii of gyration obtained from EOM modeling of datasets from three SAXS measurements at each ionic strength.

FIG. 20A-B shows (A) Experimental curves for variation of fluorescence intensity as a function of angle of incidence of excitation light for substrates functionalized with fluorescein and fluorescein labeled PEG of molecular weight 5000 Da. (B) Heights of the two layers calculated from these curves. The data presented here are the mean and standard error of the heights obtained from the three experiments.

FIG. 21 shows Sequences of the peptides used for the SAIM measurements (SEQ ID NOs: 5 and 6).

DETAILED DESCRIPTION

Figure 1A:
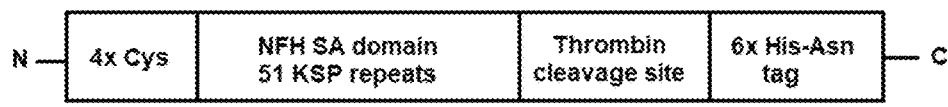
FIG. 1A-C shows characterization of rNFH-SA. (a) Domain structure of rNFH-SA showing the N-terminal tetra-Cys tag, the intrinsically disordered protein (IDP) domain and the C-terminal HN tag. The NF-H sidearm sequence lacks native cysteines, thereby allowing the use of the tetra-Cys tag for oriented assembly. (b) Far-ultraviolet CD spectrum of rNFH-SA. (c) Distribution of hydrodynamic radii (rH) obtained from dynamic light scattering.

As used herein and in the appended claims, the singular forms "a," "and," and the include plural referents unless the context clearly dictates otherwise. Thus, for example, reference to "a probe" includes a plurality of such cells and reference to the "cell" includes reference to one or more cells and equivalents thereof known to those skilled in the art, and so forth.

Also, the use of or means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. With respect to any term that is presented in one or more publications that is similar to, or identical with, a term that has been expressly defined in this disclosure, the definition of the term as expressly provided in this disclosure will control in all respects.

Intrinsically disordered proteins (IDPs) are an emerging and important class of biomolecules with unique material properties that can be integrated into biological systems. The disclosure demonstrates that such IDPs can be engineered, expressed, purified and can be used to form monodisperse, oriented brushes on surfaces. Furthermore, these brushes are shown to collapse and swell in response to changes in solution ionic strength and pH, and that they can be enzymatically shaved to defined heights through the application of proteases directed to specific sequences within the chain.

The amino acid sequence of IDPs endow them with extremely high structural flexibility, akin to synthetic polymers. This, coupled with the extensive biological applications of polymer-based materials, for example as drug delivery agents, cell culture matrices and surface-functionalization reagents for modulating interfacial properties, suggest a promising role of IDPs as bio-interfacial materials.

A unique feature, as discussed further herein, of IDP-based materials relative to synthetic heteropolymers is the ability to precisely control monomeric sequence. IDP conformational properties and resulting interfacial behavior are controlled to a large extent by electrostatic interactions between charged residues. However, unlike synthetic polymers, where charged groups are either homogenously distributed over the polymer chain length or introduced as discrete blocks, IDPs allow precise control over the position of different charged residues. Phosphorylation represents an additional mechanism to reversibly control protein charge in a site-specific and dynamic manner. This precise control on position of charge over the polymer chain endows IDPs with superior potential as elements of responsive biomaterials. In recent years atomistic simulations for IDPs have been developed that highlight the importance of charge position, distribution, and resultant local conformational preferences within an IDP chain in controlling the overall conformations of the IDP. Furthermore, enzymatic control of charge on an IDP via phosphorylation, for example, provides a biologically relevant switch with which to control the interfacial characteristics of these molecules in vivo.

The disclosure provides a protein-based polymer brush system whose conformational properties can be modulated by changes in pH and ionic strength. Notably, this material can be recombinantly expressed, forms brushes, and yields a about six- to tenfold dynamic range in brush thickness as ionic strength is varied and about a threefold range as pH is varied. This dynamic range is comparable to many existing synthetic polymer brush systems, thus providing an attractive complement or alternative to synthetic systems in specific settings. In addition, the dynamic range can be shifted, widened, or narrowed in interesting ways by exerting more control over the grafting density, such as by using cloud point grafting to achieve very dense brushes. Furthermore, proteases can be used to reduce the height of the brush in situ by cleaving the constituent chains at defined points. The extensive suite of proteases and protease recognition sites—any of which could be introduced into the sequence at one or more arbitrary positions—provides a versatile toolbox for controlling intrinsically disordered protein (IDP) brush properties in a dynamic and specific manner. Analogous enzymatically addressable materials have been explored for a variety of applications such as payload delivery, diagnostic monitoring and ligand presentation.

Polymer brushes form when macromolecular chains are end-tethered to surfaces at high grafting densities. The swelling and mutual steric repulsion of the polymers cause the chains to stretch and extend into the surrounding milieu, producing a molecular coating that can reduce non-specific interactions of the underlying surface with cells and biological macromolecules. Some polymer brushes are environment-sensitive, with specific changes in solvent conditions triggering their expansion or collapse. These materials can be used to exert dynamic control over the spatial presentation of regulatory peptides and are under investigation for many applications, including sensors, flow valves and controlled drug release systems. However, because these brushes are almost universally constructed from synthetic polymers, they are frequently somewhat heterogeneous and are challenging to modify at specific monomeric positions along the chain. While there have been notable successes integrating these materials with proteins to control biological function, such strategies require covalent conjugation of the protein to the polymer, which can be inefficient and can compromise biological function.

These limitations are overcome by the present disclosure through the creation of a class of polymer brushes based on intrinsically disordered proteins (IDPs). As mentioned above, IDPs are attractive candidates for fabricating polymer/protein brushes primarily because they lack secondary structure and adopt an extended conformation. IDPs can also be designed and purified to near-perfect homogeneity, with the naturally occurring amino acids providing a chemically diverse palette for the control of chain properties such as charge distribution and hydrophobicity. In addition, the potential to synthesize proteins with either bioactive epitopes fused to IDP segments or sequences that can be enzymatically modified with high specificity provides an elegant way to create biofunctional interfaces.

As is known, peptides and polypeptides are polymers of amino acids that contain multiple copies of the same or differing constitutional units. The number of constitutional units (e.g., amino acids) within a given peptide or polypeptide may vary widely, ranging, for example, from 5 to 10 to 25 to 50 to 100 to 1000 to 10,000 or more amino acid "units". Polypeptides or peptides for use in the disclosure may have a variety of architectures, including linear and branched architectures. Branched architectures include architectures in which two or more chains emanate from a single branch point, comb architectures (e.g., architectures having a main chain and a plurality of side chains) and dendritic architectures (e.g., arborescent and hyperbranched polypeptides), among others.

As used herein, the terms "polypeptide" and "protein" are used interchangeably, unless specified to the contrary, and according to conventional meaning, i.e., as a sequence of amino acids. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring. Polypeptides of the disclosure may be prepared using any of a variety of well-known recombinant and/or synthetic techniques, illustrative examples of which are further discussed below.

"Protein brush" or "Protein brushes," as the name suggests, contain proteins, polypeptide or peptides, one end of which is directly or indirectly tethered to a surface and another end of which is free to extend from the surface, somewhat analogous to the bristles of a brush. In the devices of the disclosure, protein brushes are employed, which have one or more types of polymeric amino acid chains (e.g., polypeptide). pH and ionic strength as well as other external environmental factors can modify the form of the polypeptide due to the side-group characteristics of each amino acid. As a result of this ability to change properties, such protein brushes are stimulus responsive. IDPs are highly flexible molecules, which do not have a defined 3D structure but behave as random coils, akin to synthetic polymers. One of the major in vivo functions of IDPs is their activity as "entropic bristles".

As used herein, "protein brush regions" are surface regions comprising a protein brush. Protein brush regions may be created by various methods, including covalent and non-covalent (e.g., physical adsorption) attachment. In one example of non-covalent attachment, a polypeptide is adsorbed onto a substrate, with, for example, a chain of amino acids interacting strongly with the surface of a substrate and the other chains of amino acids forming the brushes. For example, a polypeptide can comprise a compatible end that contacts the device surface (e.g., a polymer surface modified to for attachment) such that it becomes adsorbed to the surface. A second polypeptide chain may then be linked to the first chain.

While physical adsorption is relatively simple to carry out, covalent techniques may be used in some embodiments, due to the stability and enhanced control over the protein density, which may be afforded by such techniques. Covalent attachment of polypeptide to form protein brushes is commonly achieved by substrate modification. Such modification include providing anchoring groups on the substrate. Examples of anchoring groups include substituted or unsubstituted hydroxyl groups, thiol groups, azide groups, carboxylic acid groups, amide groups, epoxide groups, vinyl groups and trichlorosilane groups.

Each of these techniques involves the attachment of a species (e.g., a polymer or an initiator) to a surface, which may be carried out using a number of techniques that are known in the art. For instance, covalent coupling of species to a substrate surface, each having reactive functional groups, may be carried out by direct reaction between the functional groups, or through the use of linking/coupling agents that contain reactive moieties capable of reaction with such functional groups. Specific examples of known linking agents include glutaraldehyde, diisocyanates, diisothiocyanates, bis(hydroxysuccinimide)esters, maleimide-hydroxysuccinimide esters, carbodiimides, N,N'-carbonyldiimidazole imidoesters, and difluorobenzene derivatives, among others. One ordinarily skilled in the art will recognize that any number of other coupling agents may be used depending on the functional groups present.

For many substrates, including polymer substrates, surface functional groups may be introduced by treating the substrate with a reactive plasma. For example, gas discharge techniques, in which surface modification is achieved by exposing the surface to a partially ionized gas (e.g., to a plasma). Because the plasma phase consists of a wide spectrum of reactive species (electrons, ions, etc.) these techniques have been used widely for functionalization of surfaces. Two types of processes are frequently described, depending on the operating pressure: corona discharge techniques (which are conducted at atmospheric pressure) and glow discharge techniques (which are conducted at reduced pressure). Glow discharge techniques may be preferred over corona discharge techniques in certain embodiments, because the shape of the object to be treated is of minor importance during glow discharge processes. Moreover, glow discharge techniques are usually either operated in an etching or in a depositing mode, depending on the gas used, whereas corona discharge techniques are usually operated in an etching mode. A commonly employed glow discharge technique is radio-frequency glow discharge (RFGD).

Plasma treatment processes may be used to etch, crosslink and/or functionalize polymer surfaces, with these processes typically occurring simultaneously at a polymer surface that is exposed to a discharge of a non-polymerizable gas. The gas that is used primarily determines which of these processes is dominant.

One of skill in the art will readily recognize the many known methods for modifying a surface for attachment of a protein, polypeptide or peptide.

Polypeptides that can be used to form a "bristle" of a protein brush can comprise a number of different sequences. These sequences can be designed to include various amino acids with desired side groups to control the length, structure, interaction and responsiveness to the environment. The peptide/polypeptide bristles generally comprise amino acid residues linked and characterized such that do not have a tendency to form secondary structure.

In one embodiment, the disclosure describes stimuli-responsive IDPs that can be assembled onto a surface of a substrate to form a protein brush. In one embodiment, the design is based on the disordered C-terminal sidearm domain of the heavy subunit of the neurofilament complex (NF-H) (see, SEQ ID NO:1 and GenBank Accession No. NP_066554.2, incorporated herein by reference), which functions as an entropic spring that facilitates the assembly, mechanics and transport of neurofilaments (NFs) in the neuronal cytoskeleton. This subunit has two notable features: first, it contains a large and nearly equal number of cationic (Lys, Arg) and anionic (Glu, Asp) residues, rendering it highly charged locally but nominally neutral globally. Second, it consists of a series of Lys-Ser-Pro (KSP) motifs, which allows for the modulation of protein charge in vivo via phosphorylation of the Ser residues.

In another embodiment, the disclosure describes an engineered protein (rNFH-SA) comprising residues 426-1066 from the rat NF-H sidearm domain (see, e.g., SEQ ID NO:2), flanked by an N-terminal tetra-Cys tag and a C-terminal poly-His-Asn tag. The rNFH-SA adopts an extended, disordered conformation in solution and can be grafted in an oriented manner to solid supports to yield IDP brushes that swell and collapse in response to changes in solution pH and ionic strength. The heights of these brushes may be modulated through the application of proteases that recognize specific sequences within the brush.

SEQ ID NO:1 (*homo sapiens* NF-H):

```
  1  mmsfggadal lgapfaplhg ggslhyalar kggaggtrsa agsssgfhsw trtsvssvsa
 61  spsrfrgaga asstdsldtl sngpegcmva vatsrsekeq lqalndrfag yidkvrqlea
121  hnrslegeaa alrqqqagrs amgelyerev remrgavlrl gaargqlrle qehllediah
181  vrqrlddear qreeaeaaar alarfaqeae aarvdlqkka qalqeecgyl rrhhqeevge
241  llgqiqgsga aqaqmqaetr dalkcdvtsa lreiraqleg havqstlqse ewfrvrldrl
301  seaakvntda mrsaqeeite yrrqlqartt elealkstkd slerqrsele drhqadiasy
361  qeaiqqldae lrntkwemaa qlreyqdlln vkmaldieia ayrkllegee crigfgpipf
421  slpeglpkip svsthikvks eekikvveks eketviveeq teetqvteev teeeekeake
481  eegkeeegge eeeaeggeee tksppaeeaa spekeakspv keeakspaea kspekeeaks
541  paevkspeka kspakeeaks ppeakspeke eakspaevks pekakspake eakspaeaks
601  pekakspvke eakspaeaks pvkeeakspa evkspekaks ptkeeakspe kakspekeea
661  kspekakspv kaeakspeka kspvkaeaks pekakspvke eakspekaks pvkeeakspe
721  kakspvkeea ktpekakspv keeakspeka kspekaktld vkspeaktpa keearspadk
781  fpekakspvk eevkspekak splkedakap ekeipkkeev kspvkeeekp qevkvkeppk
841  kaeeekapat pkteekkdsk keeapkkeap kpkveekkep avekpkeskv eakkeeaedk
901  kkvptpekea pakvevkeda kpkektevak kepddakake pskpaekkea apekkdtkee
961  kakkpeekpk teakakeddk tlskepskpk aekaekssst dqkdskppek atedkaakgk
```

SEQ ID NO:2 (*Rattus norvegicus* NF-H):

```
  1  mmsfgsadal lgapfaplhg ggslhyalsr kagaggtrsa agsssgfhsw artsvssvsa
 61  spsrfrgaas stdsldtlsn gpegcvaava arsekeqlqa lndrfagyid kvrqleahnr
121  tlegeaaalr qqkgraamge lyerevremr gavlrlgaar ghvrleqehl lediahvrqr
181  ldeearqree aeaaaralar faqeaeaarv elqkkaqalq eecgylrrhh qeevgellgq
241  iqgcgaaqaq aqaeardalk cdvtsalrei raqleghtvq stlqseewfr vrldrlseaa
301  kvntdamrsa qeeiteyrrq lqarttelea lkstkesler qrseledrhq vdmasyqdai
361  qqldnelrnt kwemaaqlre yqdllnvkma ldieiaayrk llegeecrig fgpspfslte
421  glpkipsmst hikvkseeki kvvekseket viveeqteei qvteevteee dkeaggeeee
481  eaeeggeeaa ttsppaeeaa speketkspv keeakspaea kspaeakspa eakspaevks
541  paevkspaea kspaeakspa evkspatvks paeakspaea kspaevkspa tvkspgeaks
601  paeakspaev kspveakspa eakspasvks pgeakspaea kspaevkspa tvkspveaks
661  paevkspvtv kspaeakspv evkspasvks pseakspaga kspaeakspv vakspaeaks
721  paeakppaea kspaeakspa eakspaeaks paeakspvev kspekakspv kegakslaea
781  kspekakspv keeikppaev kspekakspm keeakspeka ktldvkspea ktpakeeakr
841  padirspeqv kspakeeaks pekeetrtek vapkkeevks pveevkakep pkkveeektp
```

```
 901    atpktevkes kkdeapkeaq kpkaeekepl tekpkdspge akkeeakekk aaapeeetpa 961    klgvkeeakp kekaedakak epskpsekek pkkeevpaap ekkdtkeekt teskkpeekp 1021    kmqakakeed kglpqepskp ktekaeksss tdqkdsqpse kapedkaakg dk
```

In one embodiment, the protein bristle can comprise a sequence that is at least 90-100% identical to SEQ ID NO:1 or 2. In another embodiment, the protein bristle comprises a sequence that is a fragment of SEQ ID NO:1 or 2 and comprises at least 90-100% identity to SEQ ID NO:1 or 2. In still another or further embodiment, the protein bristle can comprise one or more additional domains. For example, as set forth above, the bristle can comprise a sequence and/or fragment having identity to SEQ ID NO:1 or 2 and can include at least one additional domain selected from the group consisting of (a) a protease cleavage site, (b) a purification domain, (c) a spacer sequence, (d) a further domain having a sequence 90-100% identical to SEQ ID NO:1 or 2 separated by (a), (b) and/or (c), and any combination of the foregoing. In one embodiment, the polypeptide is charge neutral (e.g., the total charge of each amino acid in the polypeptide added up results in a net neutral polypeptide). In a further embodiment, the charge neutral polypeptide can comprise phosphorylatable amino acids that can be phosphorylated or de-phosphorylated in order to modulate the charge of the polypeptide. In another embodiment, a first end of the polypeptide can be linked or conjugated to a surface and the second end of the polypeptide is free. In a further embodiment, the second end extends substantially vertically from the surface (e.g., a planar surface) of the substrate under conditions that promote extension of the polypeptide. In another embodiment, the polypeptide can have a plurality of domains (e.g., a domain substantially identical to SEQ ID NO:1 or 2 and a second domain comprising a protease cleavage site). In another embodiment, the second end of the polypeptide (e.g., the free end) can comprise a domain or moiety that promotes binding or interaction with a device or biological factor.

FIG. 1 depicts an example of a protein bristle of the disclosure. One of skill in the art will recognize that a number of variations can be made to the bristle using techniques known in the art. Further, recombinant methods, techniques for producing such "bristles", are known in the molecular/recombinant DNA field. Alternatively, the bristle can be synthesized using well known peptide synthesis techniques, reagents and device.

Using a solid-phase peptide synthesizer, various types of "bristle" polypeptides can be generated. For example, the disclosure demonstrates the generation of two 32-residue peptides based on the NF-H sidearm domain. The first peptide contained four KSP motifs (KSP peptide), while in the second the serine residues were replaced with aspartate residues (KDP peptide) (FIG. 15A). Comparison of the KSP and KDP peptides provides an insight into electrostatic effects associated with changes in chain charge on IDP structure and stimulus-responsiveness. Additionally, as aspartate residues are sometimes used to mimic effects of phosphorylation in proteins, these bristles provide insight into how serine phosphorylation in these sidearm domains contributes to NF structure and interactions in the cytoskeleton A variety of devices and portions thereof may be provided with protein brush regions including, for example, catheters (e.g., renal or vascular catheters), balloons, catheter shafts, guide wires, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, patches, pacemakers and pacemaker leads, heart valves, vascular valves, tissue engineering scaffolds for cartilage, bone, skin and other in vivo tissue regeneration, and so forth.

The protein brushes may be provided over the entire surface of the medical device or over only a portion of the medical device surface. For example, with tubular devices such as stents, protein brushes may be provided over the entire surface of the stent, or they may be provided on the inner luminal surface of the stent, on the outer abluminal surface of the stent, and/or on the lateral surfaces between the luminal and abluminal surfaces (including the ends). The protein brushes may be provided in desired patterns, for instance, using appropriate masking techniques. As another example, protein brushes may be provided over some device components but not others (e.g., over the balloon of a balloon catheter, but not over the catheter shaft).

For example, it is known that adhesion between a balloon and surrounding stent can lead to an increase in the force that is needed for balloon withdrawal. The use of the brushes of the disclosure can reduce the needed force by coating the balloon or lumen of the catheter/stent with the polypeptides described herein.

An advantage of a protein brush surface having both hydrophilic and hydrophobic chains is that the surface will reorient once it is exposed to an aqueous environment, resulting in a surface that is primarily composed of hydrophilic chains such that a hydrophilic surface is presented to the surrounding environment. Therefore, the device biocompatibility will actually change after the device is deployed.

Protein brush regions may be provided over a number of medical device substrates. Materials for use as underlying medical device substrates include (a) organic materials (e.g., materials containing 50 wt % or more organic species) such as polymeric materials and (b) inorganic materials (e.g., materials containing 50 wt % or more inorganic species), such as metallic materials (e.g., metals and metal alloys) and non-metallic materials (e.g., including carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others).

Specific examples of non-metallic inorganic materials may be selected, for example, from materials containing one or more of the following: metal oxides, including aluminum oxides and transition metal oxides (e.g., oxides of titanium, zirconium, hafnium, tantalum, molybdenum, tungsten, rhenium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based, ceramic-like materials such as carbon nitrides.

Specific examples of metallic inorganic materials may be selected, for example, from metals (e.g., biostable metals such as gold, platinum, palladium, iridium, osmium, rhodium, titanium, tantalum, tungsten, and ruthenium, and bioresorbable metals such as magnesium) and metal alloys, including metal alloys comprising iron and chromium (e.g., stainless steels, including platinum-enriched radiopaque stainless steel), alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), and alloys comprising nickel and chromium (e.g., inconel alloys).

Specific examples of organic materials may be selected, for example, from the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides and polyether block amides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-alkylene copolymers, including styrene-butadiene copolymers, styrene-ethylene-butylene copolymers (e.g., a polystyrene-polyethylene/butylene-polystyrene (SEBS) copolymer, available as Kraton®. G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk), polyvinyl ketones, polyvinylcarbazoles, and polyvinyl esters such as polyvinyl acetates; polybenzimidazoles; ethylene-methacrylic acid copolymers and ethylene-acrylic acid copolymers, where some of the acid groups can be neutralized with either zinc or sodium ions (commonly known as ionomers); polyalkyl oxide polymers and copolymers including polyethylene oxides (PEG); polyesters including polyethylene terephthalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly (caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as further copolymers and blends of the above.

Where implantable or insertable medical devices are provided which contain protein brush regions that regulate the release of therapeutic agents, the release profile associated with such devices may be modified, for example, by changing the chemical composition, size, and/or number of the protein brush regions on the device, among other parameters. For example, the release profile may be affected by the concentration of therapeutic agent(s) within the protein brush region(s), by the amino acid composition of the protein brush region(s), by the surface area of the protein brush region(s), and so forth. Multiple protein brush region(s), having either the same content or different content (e.g., different protein and/or therapeutic agent content), may be provided on the medical device surfaces. Hence, protein brush region(s) may be adapted to release the same or different therapeutic agents, at the same or different rates, from different locations on the medical device. For instance, a tubular medical device (e.g., a vascular stent) may be provided which has a protein brush region that contains or is disposed over an antithrombotic agent at its inner, luminal surface and a second protein brush region which contains or is disposed over therapeutic agents at its outer, abluminal surface (as well as on the ends, if desired).

As noted above, a medical devices of the disclosure can optionally contain one or more therapeutic agents. "Therapeutic agents," "drugs," "pharmaceutically active agents," "pharmaceutically active materials," and other related terms may be used interchangeably herein. These terms include genetic therapeutic agents, non-genetic therapeutic agents and cells.

Therapeutic agents include, for example, adrenergic agents, adrenocortical steroids, adrenocortical suppressants, alcohol deterrents, aldosterone antagonists, amino acids and proteins, ammonia detoxicants, anabolic agents, analeptic agents, analgesic agents, androgenic agents, anesthetic agents, anorectic compounds, anorexic agents, antagonists, anterior pituitary activators and suppressants, anthelmintic agents, anti-adrenergic agents, anti-allergic agents, anti-amebic agents, anti-androgen agents, anti-anemic agents, anti-anginal agents, anti-anxiety agents, anti-arthritic agents, anti-asthmatic agents, anti-atherosclerotic agents, antibacterial agents, anticholelithic agents, anticholelithogenic agents, anticholinergic agents, anticoagulants, anticoccidal agents, anticonvulsants, antidepressants, antidiabetic agents, antidiuretics, antidotes, antidyskinetics agents, anti-emetic agents, anti-epileptic agents, anti-estrogen agents, antifibrinolytic agents, antifungal agents, antiglaucoma agents, antihemophilic agents, antihemophilic Factor, antihemorrhagic agents, antihistaminic agents, antihyperlipidemic agents, antihyperlipoproteinemic agents, antihypertensives, antihypotensives, anti-infective agents, anti-inflammatory agents, antikeratinizing agents, antimicrobial agents, antimigraine agents, antimitotic agents, antimycotic agents, antineoplastic agents, anti-cancer supplementary potentiating agents, antineutropenic agents, antiobsessional agents, antiparasitic agents, antiparkinsonian drugs, antipneumocystic agents, antiproliferative agents, antiprostatic hypertrophy drugs, antiprotozoal agents, antipruritics, antipsoriatic agents, antipsychotics, antirheumatic agents, antischistosomal agents, antiseborrheic agents, antispasmodic agents, antithrombotic agents, antitussive agents, anti-ulcerative agents, anti-urolithic agents, antiviral agents, benign prostatic hyperplasia therapy agents, blood glucose regulators, bone resorption inhibitors, bronchodilators, carbonic anhydrase inhibitors, cardiac depressants, cardioprotectants, cardiotonic agents, cardiovascular agents, choleretic agents, cholinergic agents, cholinergic agonists, cholinesterase deactivators, coccidiostat agents, cognition adjuvants and cognition enhancers, depressants, diagnostic aids, diuretics, dopaminergic agents, ectoparasiticides, emetic agents, enzyme inhibitors, estrogens, fibrinolytic agents, free oxygen radical scavengers, gastrointestinal motility agents, glucocorticoids, gonad-stimulating principles, hemostatic agents, histamine H2 receptor antagonists, hormones, hypocholesterolemic agents, hypoglycemic agents, hypolipidemic agents, hypotensive agents, HMGCoA reductase inhibitors, immunizing agents, immunomodulators, immunoregulators, immunostimulants, immunosuppressants, impotence therapy adjuncts, keratolytic agents, LHRH agonists, luteolysin agents, mucolytics, mucosal protective agents, mydriatic agents, nasal decongestants, neuroleptic agents, neuromuscular blocking agents, neuroprotective agents, NMDA antagonists, non-hormonal sterol derivatives, oxytocic agents, plasminogen activators, platelet activating factor antagonists, platelet aggregation inhibitors, post-stroke and post-head trauma treatments, progestins, prostaglandins, prostate growth inhibitors, prothyrotropin agents, psychotropic agents, radioactive agents, repartitioning agents, scabicides, sclerosing agents, sedatives, sedative-hypnotic agents, selective adenosine A1 antagonists, serotonin antagonists, serotonin inhibitors, serotonin receptor antagonists, steroids, stimulants, thyroid hormones, thyroid inhibitors, thyromimetic agents, tranquilizers, unstable angina agents, uricosuric agents, vasoconstrictors, vasodilators, vulnerary agents, wound healing agents, xanthine oxidase inhibitors, and the like.

In addition, the protein brush technology described herein can be used to coat a biological molecule or drug. For example, protein brushes comprising intrinsically disordered proteins (IDP) can be used to interfer/modulate protein-protein interactions (PPI). In this model, an intrinsically disordered domain of a folded protein, or an IDP fused to a folded functional protein of interest (POI), by virtue of its flexibility, can cover a large space around its attachment point, and thus create a region of exclusion around its partner. This restricts larger molecules such as proteins from the proximity, while salts and cofactors should not be excluded. Thus, the IDP creates an "entropic cage" which impedes the POI from interacting with its partner thereby preventing protein-protein interaction. Naturally occurring examples of such systems are the intrinsically disordered domains of neurofilament proteins that control neurofilament-spacing, and the projection domains of tau protein that control the distance between microtubules. Another example is the C-terminal disordered domain of Knr4 (a yeast "hub" protein interacting with more than 30 distinct proteins), which strongly attenuates the interaction of Knr4 with its interaction partners. Thus, intrinsically disordered regions as entropically-driven perturbers of PPIs have been established for some isolated cases.

Figure 22:
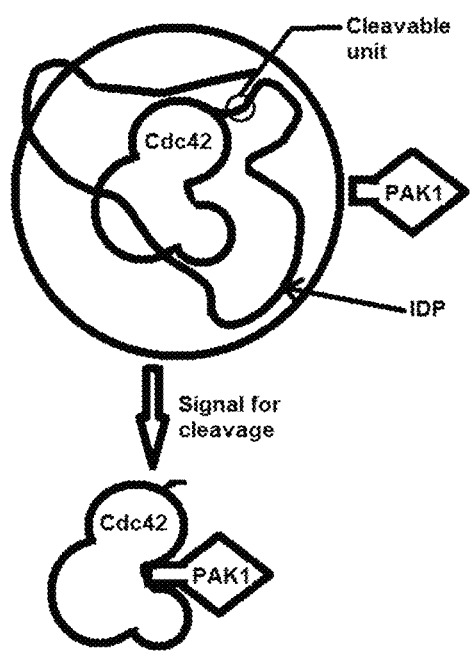
FIG. 22 shows an IDP creates a region of exclusion (entropic cage) around a protein of interest (POI) preventing protein-protein interactions (PPIs). Introduction of a cleavage signal removes the IDP and uncages the POI.

Based on these observations, IDPs can be used to control PPIs. In one embodiment, one or more IDPs for a bristle or brush on a protein of interest via a cleavable linker (protease cleavage site, photocleavable amino acid etc.) so as to "cage" the POI and completely abrogate its interaction with native interaction partners (FIG. 22). Upon introduction of the appropriate cleavage signal, the IDP is cleaved off and the POI is "uncaged" and free to interact with its interaction partners. Such techniques would be useful for targeted delivery of a drug or biologic to a selected are in vitro or in vivo.

Although much effort has focused on understanding the biological function of endogenous IDPs, the disclosure demonstrates that IDPs represent an untapped resource for biomaterial design. IDPs can be used as biosynthetic coatings, fusion proteins whose functions may be sterically gated, and novel cell surface engineering strategies. As described herein, IDPs can be designed de novo, synthesized at high purity, and chemically tailored at specific positions along the chain through mutagenesis. IDP sequences can be optimized for specific applications through directed-evolution approaches and synthesized to include bio-orthogonal chemical moieties via the use of unnatural amino acids. Indeed, IDPs based on nucleoporin proteins have recently been incorporated into synthetic gated pores and surface-grafted layers, supporting the idea that IDPs can be manipulated in ways that are analogous to synthetic polymers. Together with these efforts, our work hints at the value of exploring IDPs as a new class of "smart" biomaterial building blocks.

The disclosure is illustrated in the following examples, which are provided by way of illustration and are not intended to be limiting.

EXAMPLES

Example 1

Cloning and expression of rNFH-SA. Expression vectors were constructed by modifying the multiple cloning site of pET6xHN-C (Clontech Inc.) to include the EcoR1 and HindIII restriction enzyme recognition sequences. The modified expression vector was digested with EcoR1 and HindIII and subsequently purified. A HindIII restriction enzyme site was introduced at the end of NFH-SA gene cloned in pCIneo by site-directed mutagenesis. The modified NFH-SA gene was excised from the pCIneo vector by EcoR1 and HindIII digestion, ligated to the linearized, modified pET6xHN-C vector, and transformed into competent *Escherichia coli* cells. Plasmids isolated from the resulting transformants were screened by a diagnostic restriction enzyme digestion and sequenced.

The expression vector was transformed into the *E. coli* Rosetta strain (Novagen) for expression. Confluent starter cultures (grown overnight) were transferred to expression cultures and incubated with shaking at 37° C. Expression was induced by the addition of isopropyl b-D-1-thiogalactopyranoside to a final concentration of 0.75 mM. The cells were typically harvested 3 h after induction by centrifugation at 3,000 g for 20 min at 4° C.

Purification of rNFH-SA. The cell pellet was resuspended in 20 mM Tris pH 8.0, 300 mM NaCl, 1 mM tris(2-carboxyethyl)phosphine hydrochloride (TCEP), 1 mM phenylmethanesulfonylfluoride and lysed by sonic disruption at 4° C. The cell lysate was centrifuged at 20,000 g for 15 min at 4° C. to remove insoluble cellular matter and then applied to a nickel-nitrilotriacetic acid affinity column. After subsequent washes with increasing concentration of imidazole, the purified protein was eluted using 200 mM imidazole. Ion exchange chromatography using a linear elution gradient of increasing ionic strength over a diethylaminoethyl cellulose anion exchange resin was used as a polishing step to improve purity when needed.

Circular dichroism. CD spectra were recorded from 250 to 190 nm on a Jasco-720 spectropolarimeter. Spectra were obtained using a cuvette with a 1-mm path length at 25° C. at a bandwidth of 1 nm with a scanning rate of 10 nm s$^{-1}$ in continuous scanning mode and a response time of 5 s. The collected raw spectra were buffer subtracted and converted from millidegrees to molar ellipticity. To study the protein under different solution conditions, the protein was desalted into distilled water, lyophilized and then re-dissolved in the appropriate pH/ionic strength solution. Appropriate controls were included to ensure that desalting and lyophilization did not introduce conformational changes.

The solutions used in this study include water at pH 2.4, 6.3 and 10.9, and water with 50 mM NaCl at pH 2.4 and 10.9.

Dynamic light scattering. Dynamic light scattering experiments were performed on a Dynapro Nanostar (Wyatt Technology, Santa Barbara, Calif., USA) operating at 658 nm. Measurements were performed at room temperature (25° C.) in triplicates, in 20 mM Tris pH 8.0, 1 mM TCEP. All data were analyzed using a dedicated software package (Dynamics, version 7.1, Wyatt Technology). To study the effect of different solution conditions, the protein solution was prepared as described for circular dichroism.

Figure 4:
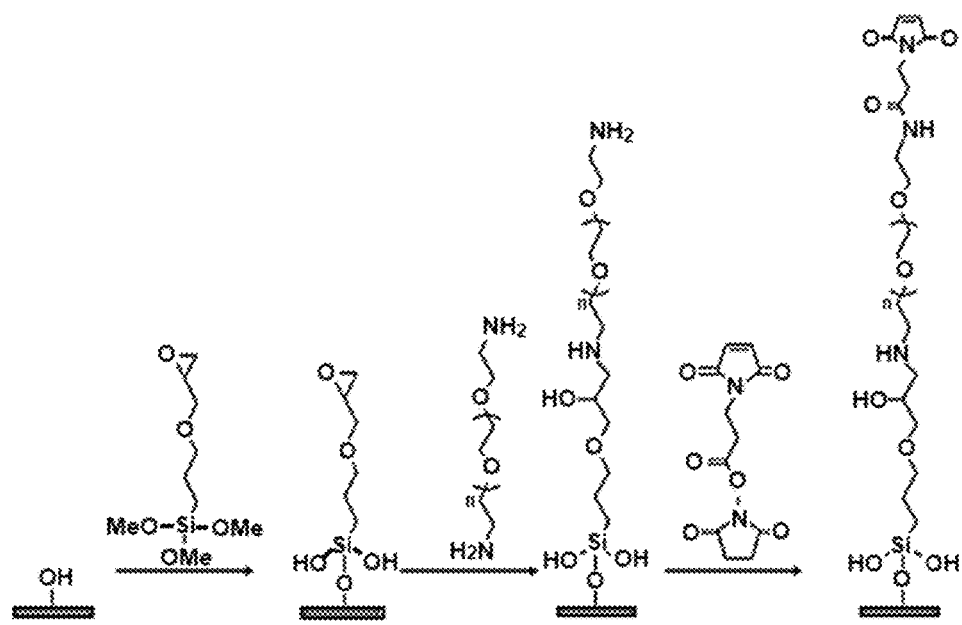
FIG. 4 shows surface modification strategy. Functionalization of silica surfaces to generate maleimide groups for oriented attachment of proteins.

Functionalization of silica and quartz surfaces. Functionalization of silica coverslips for AFM, quartz substrates for QCM-D experiments and silicon substrates for ellipsometry were carried out as described by Waichman et al. (Anal. Chem. 82, 1478-1485 (2010)). Substrates were activated via plasma cleaning prior to functionalization. After rinsing with water and drying in a nitrogen stream, the surfaces were subsequently silanized with glycidyloxypropyltrimethoxysilane (GOPTS) for 45 min at 75° C. The surfaces were then rinsed with acetone and reacted with diamino-polyethylene glycol (molecular weight of 400 Da) for 4 h at 75° C. After rinsing with water and drying in a nitrogen stream, the surface amines were reacted with a saturated solution of 3-(Maleimido)propionic acid N-hydroxysuccinimide ester (NHS-maleimide) in dry dimethylformamide for 45 min at room temperature to yield maleimide-functionalized surfaces. This sequence of reactions is shown in FIG. 4. Substrates for AFM and ellipsometry experiments were subsequently incubated under a 5 mg ml-1 solution of rNFH-SA in phosphate buffered saline (PBS) for 20 h followed by rinsing in PBS.

Quartz crystal microbalance with dissipation. QCM-D measurements were performed with a Q-Sense E4 system. Quartz crystals with fundamental frequencies of B5 MHz were functionalized as described in the previous section and used for immobilization of rNFH-SA. Either 0.5 or 5 mg ml$^{-1}$ of the rNFH-SA solution was prepared in PBS at pH 7.5 and injected into the flow cell with a rate of typically 50 ml min$^{-1}$, using a syringe pump. Change in frequency (Df) and dissipation (DD) were measured at five overtones (n ¼ 3, 5 y 11) simultaneously. After an initial binding was observed, the pump was turned off and the protein was incubated on the surface for either 4 h (0.5 mg ml$^{-1}$) or 20 h (5 mg ml$^{-1}$) depending on the protein concentration. The adsorbed protein on the crystal was then washed with buffer to remove any non-specifically bound material. The data were fit using the Voight-Voinova model for viscoelastic films to obtain the mass of the hydrated protein layer bound to the surface.

Spectroscopic ellipsometry. Silicon wafers (University-Wafer, Inc.) were cut into 1 cm$^2$ pieces for use as SE substrates. The substrates were functionalized as described herein. SE measurements were conducted on an alpha-SE system (J.A. Woollam Co., Inc.) at an angle of incidence of 70° in the spectral range of 380 to 890 nm under air at room temperature. Data was collected on surfaces functionalized with the NHS-maleimide cross-linker to model the underlying surface chemistry consisting of GOPTS, diaminopolyethylene glycol and the cross-linker. The height and refractive index obtained from this analysis was then used to model the data collected on surfaces functionalized with the rNFH-SA. Ellipsometric data were modelled using the CompleteEASE software.

Modeling of SE data and calculation of surface density. All spectroscopic ellipsometry (SE) data were modeled using the CompleteEASE software (J.A. Woollam Co., Inc). The refractive indices, of the surface layers were described using the Cauchy dispersion model as:

$$n = A + \frac{B}{\lambda^2} + \frac{C}{\lambda^4} \quad (1)$$

where A, B and C are fitting parameters and is the wavelength. SE data from substrates functionalized with glycidyloxypropyltrimethoxysilane (GOPTS), diamino-polyethylene glycol (DAPEG) and 3-(Maleimido)propionic acid N-hydroxysuccinimide ester crosslinker were first analyzed using an optical model consisting of one Cauchy layer on top of a silicon substrate. Note that the layer of SiO2 formed on the substrate is also included within this Cauchy layer. The optical parameters (A, B and C) as well as the thickness derived from this fitting were subsequently used for analyzing the data from substrates functionalized with rNFH-SA. For these data, the optical model consisted of two Cauchy layers on top of a silicon substrate. The parameters for the lower layer were fixed at the values obtained from the previous exercise. This analysis gave us the refractive index (n=1.38 at 632.8 nm) and thickness (t=2.29 nm) of the rNFH-SA layer. This refractive index was used to calculate the volume fraction of rNFH-SA ($f_p$) in the layer using the Brugemann effective medium approximation, which is described for this composite system by:

$$f_p \frac{(n_p^2 - n_{eff}^2)}{(n_p^2 + 2n_{eff}^2)} + (1 - f_p) \frac{(n_a^2 - n_{eff}^2)}{(n_a^2 + 2n_{eff}^2)} = 0 \quad (2)$$

Here, $n_p$, $n_a$ and $n_{eff}$ refer to the refractive indices of pure protein, air and the composite layer respectively. Using $n_p=1.55$, $n_a=1$ and $n_{eff}=1.38$, $f_p$ was calculated to be 0.71.

Having obtained the volumetric density, the surface density ($\Gamma$) could be calculated as $$\Gamma = \frac{f_p \cdot t \cdot \rho_p \cdot N_A}{M_w \cdot 10^{21}} \quad (3)$$

where $t=2.29$ nm is the thickness of the rNFH-SA layer as calculated above, $\rho_p=1.41$ g ml$^{-1}$ is the density of pure protein, $N_A$ is Avogadro's number and $M_w=70$ kDa is the molecular weight of rNFH-SA. The inter-chain distance, S was calculated to be 7.75 nm from the surface density ($\Gamma=0.02$ nm$^{-2}$) using the relation $$S = \sqrt{\frac{2}{\sqrt{3}\Gamma}} \quad (4)$$

For hexagonal close packed surface layers.

Atomic force microscopy. Force measurements were made using a Molecular Force Probe three-dimensional instrument (MFP, Asylum Research, Inc.). The experimental setup uses an open cell arrangement with a wetted tip brought into contact with the wetted sample surface. Silicon nitride cantilevers (OTR4-10) calibrated using the thermal method built into the MFP with a nominal spring constant of 0.02 N m$^{-1}$ were used. The tips had a radius of curvature of o20 nm. Force curves were typically collected over 500 nm with at least 2,048 data points per curve, at a rate of 1 Hz. Relative triggers of up to 4 nN were used to prevent the tip from damaging the surface. When exchanging solutions of different ionic strength, both the sample and tip were rinsed with several millilitres of the new solution prior to a measurement. At least 400 force curves were recorded for each sample at different points on the surface. The brush height was measured as the tip-sample separation at which the force began to increase from zero. Briefly, the raw AFM data (deflection error versus sensor displacement) was converted to force-distance curves (force versus tip-sample separation) as described by Cappella et al. The contact region was fit to a straight line and the point of hard contact was identified. The force profile at large separation was averaged to a baseline value, and the tip-sample separation at the first point where the force deviated significantly (at least three times the s.d. of the baseline fit) from the baseline value was denoted as the brush height. All of the above procedures were performed in MATLAB.

Protease digestion. The protein brush was incubated either with thrombin (1 U ml$^{-1}$, GE Healthcare) or clostripain (43 U ml$^{-1}$, Worthington Biochemicals). Thrombin was prepared in PBS pH 7.4 and clostripain was prepared in its activation buffer containing 25 mM phosphate, 1 mM calcium acetate and 2.5 mM dithiothreitol. The surface was spotted in triplicates with both 1 and 0.5 ml of enzyme and allowed to incubate overnight at room temperature. A 1 ml spot of both buffer and bovine serum albumin (1 mg ml$^{-1}$) were included as controls. The surface was stained with a primary antibody targeted towards the HN tag on rNFH-SA and the appropriate fluorescent secondary antibody. The surface was imaged using a Typhoon scanner to obtain fluorescence images. For AFM experiments, the surface was prepared with 3 ml spots each of the enzyme, corresponding buffer and water at pH 10.9. The surface was washed after overnight incubation and all subsequent measurements were performed in water at pH 10.9. The height measured on the water-incubated spot functioned as a control to ensure that incubation in the buffer did not affect the brush height.

Figure 1B:
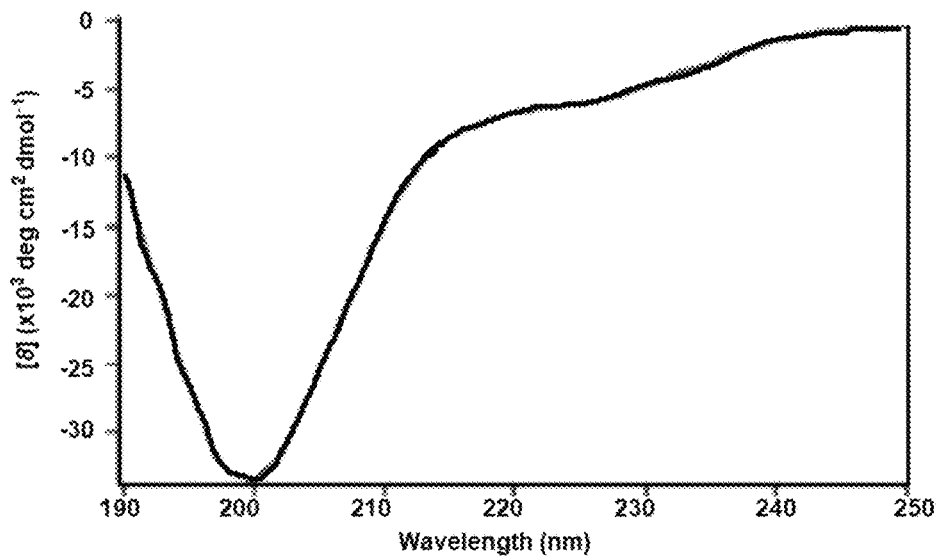
Figure 1C:
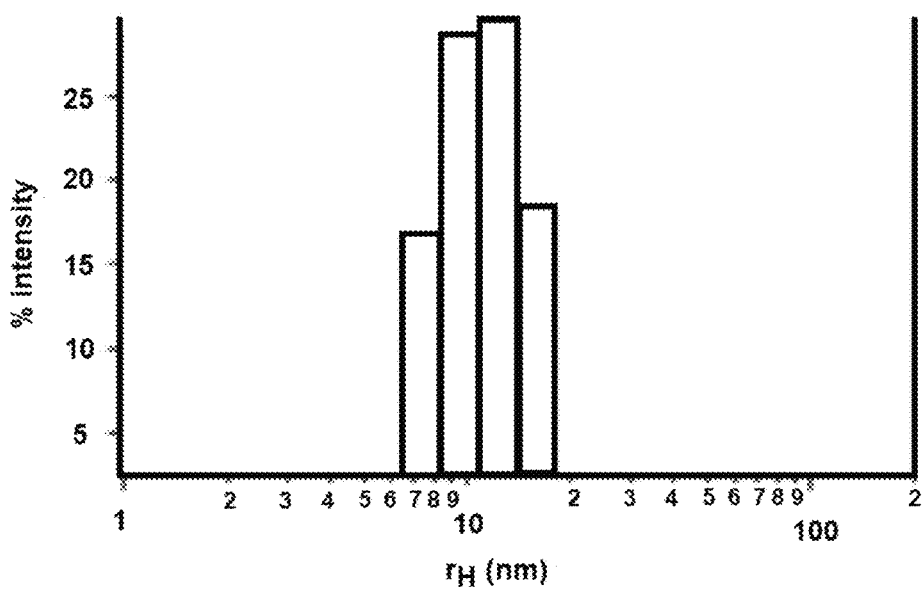
Figure 2:
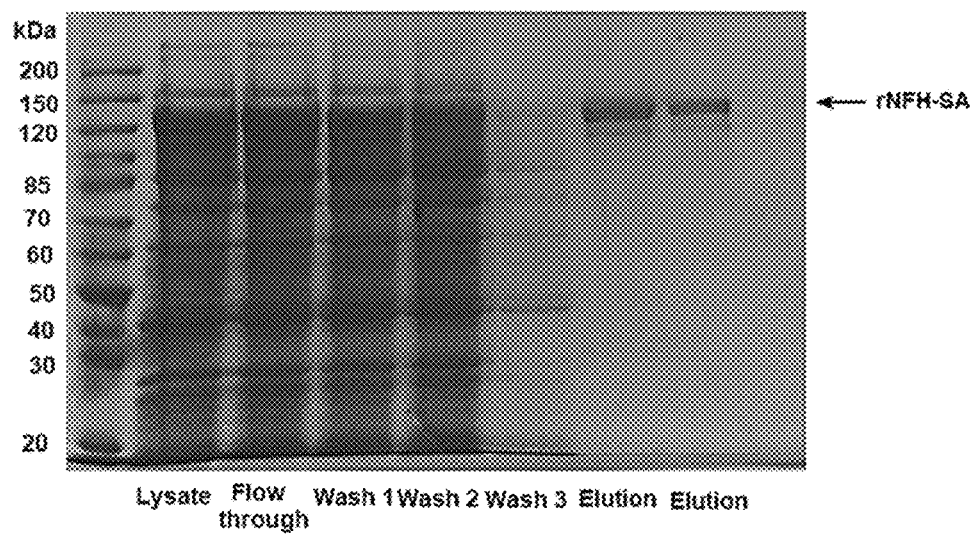
FIG. 2 shows purification of rNFH-SA. Coomassie stained SDS-PAGE illustrating purification of rNFH-SA on a Ni-NTA affinity column. In addition to the molecular weight ladder (lane 1), we show PAGE of crude cellular lysate (lane 2), material collected following application of this lysate to the column ("flow through", lane 3), material collected following a series of column washes with buffer containing increasing concentrations of imidazole (lanes 4-6), and finally material eluted from the column following application of buffer containing 200 mM imidazole (lanes 7-8).
Figure 3:
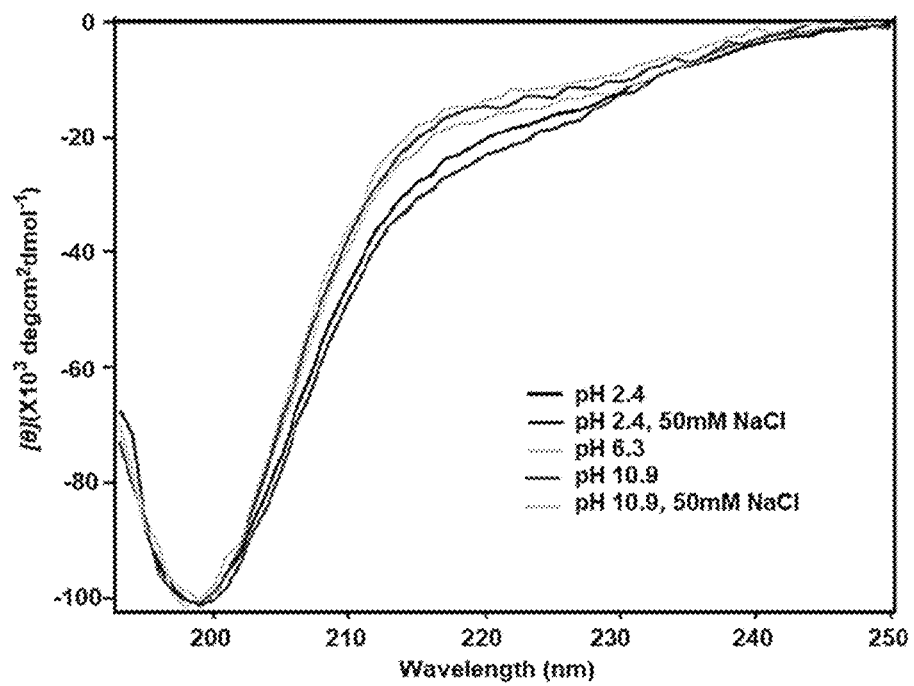
FIG. 3 shows the effect of pH and ionic strength on the secondary structure of rNFH-SA. Far-UV CD spectrum of rNFH-SA measured under different solution conditions is shown; pH 10.9, pH 6.3, pH 2.4, pH 10.9 50 mM NaCl, and pH 2.4 50 mM NaCl.

Purification and characterization of rNFH-SA. The disclosure is exemplified with a protein construct, rNFH-SA, containing residues 426-1066 from the rat NF-H sidearm domain, flanked by an N-terminal tetra-Cys tag to permit oriented assembly onto thiol-reactive surfaces and a C-terminal poly-His-Asn tag (HN-tag) to facilitate purification (FIG. 1a and FIG. 2). The circular dichroism (CD) spectrum of rNFH-SA (FIG. 1b) was consistent with that of an IDP, characterized by a minimum centered around 200 nm with negligible contribution from secondary structure-forming elements. Dynamic light scattering (DLS) measurements yielded a hydrodynamic radius ($r_H$) of 10 nm, significantly larger than the expected radius of globular proteins ($r_H$ ti 4 nm) of similar molecular weight, indicating that the protein adopts an extended conformation (FIG. 1c, FIG. 3 and Table 1).

TABLE 1

Comparison of hydrodynamic radii (rH). The rH of a hypothetical protein with a molecular mass of ~70 kDa in different conformational states is compared to that of rNFH-SA (rH = 10 nm).

| Conformational state | $r_H$, nm |
| --- | --- |
| Native | 3.7 ± 1.9 |
| Molten globule | 3.9 ± 1.4 |
| Pre-molten globule | 5.9 ± 4.1 |
| Urea denatured | 7.6 ± 1.3 |
| Guanidinium chloride denatured | 8.2 ± 1.0 |
| Native unfolded coil | 7.0 ± 0.93 |
| Native unfolded pre-molten globule | 5.3 ± 1.1 |

Figure 5A:
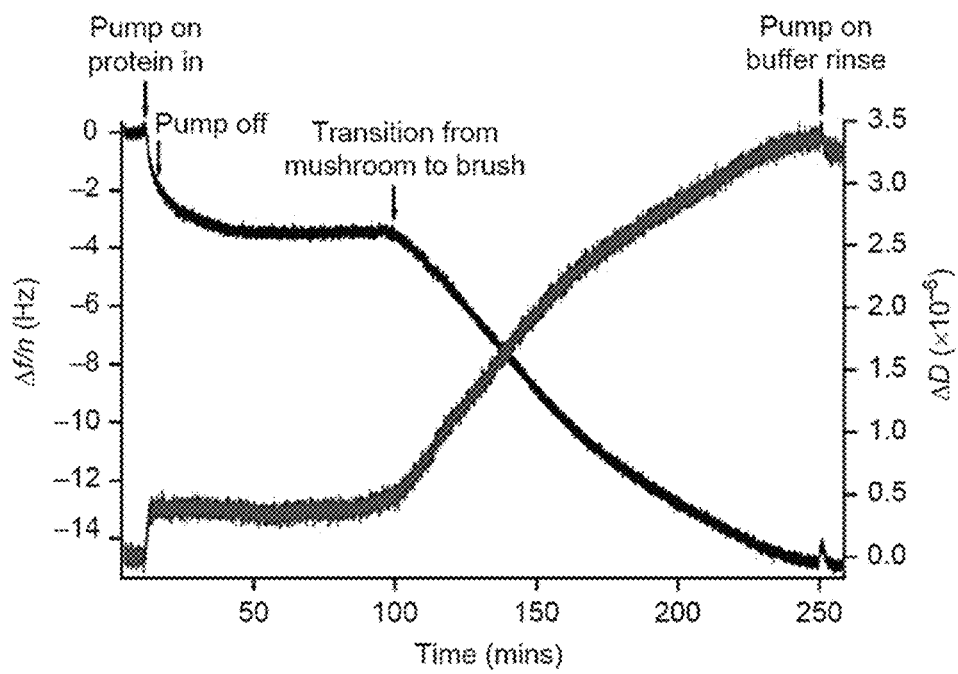
FIG. 5A-B shows brush formation observed by QCM-D measurements. (a) Df/n and DD for the overtone n ¼ 3 as a function of time obtained by QCM-D experiments. A protein concentration of 0.5 mg ml-1 was used to capture the transition from a collapsed 'mushroom' to an extended 'brush' regime. The protein solution was allowed to enter the chamber containing the functionalized sensor and subsequently allowed to stand in the chamber for B4 h. Finally, buffer was introduced into the chamber to wash away unbound protein. (b) DD versus-Df/n trace showing a sharp change in trend at B100 min. A steep slope at later time points indicates that the thickness increases significantly with grafting density and that the chains adopt an extended conformation.
Figure 5B:
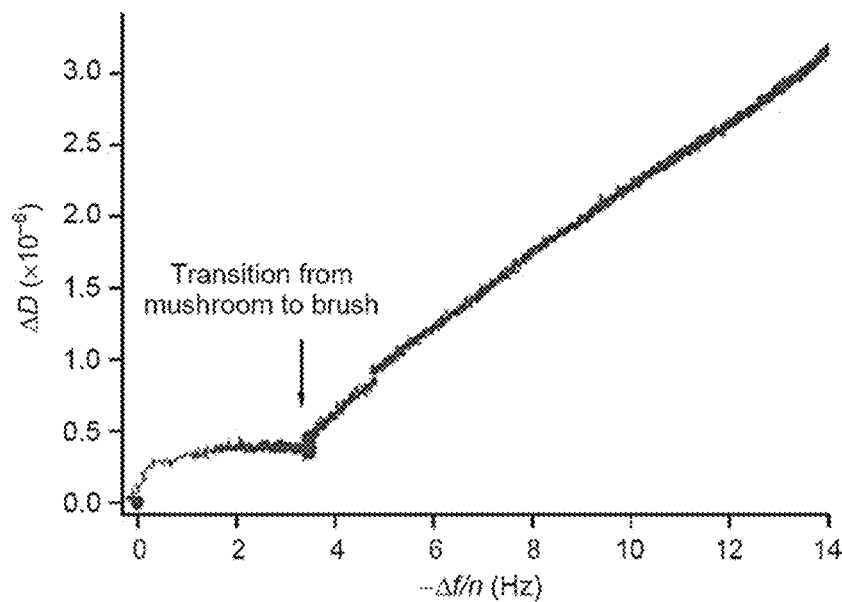
Figure 6:
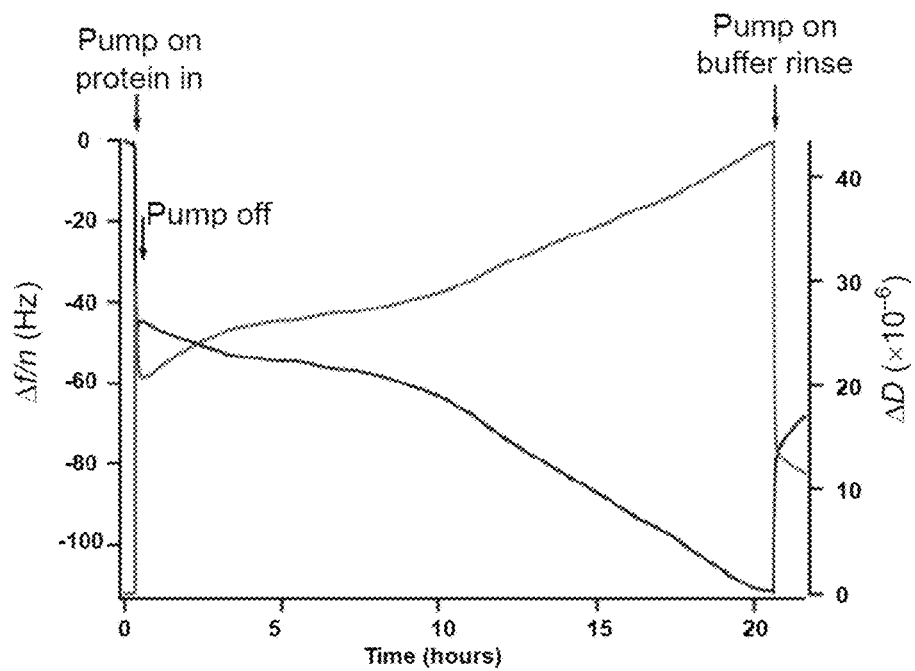
FIG. 6 shows protein binding followed by QCM-D. Δf/n and ΔD for the overtone n=3 as a function of time obtained by QCM-D experiments are shown. A protein concentration of 5 mg ml$^{-1}$ was used and the sample was incubated in the chamber for ~20 hours in order to saturate the binding sites on the surface and achieve maximum surface density. A buffer rinse was included as the final step to remove any unbound protein from the surface.

Brush Formation by Surface Immobilized rNFH-SA. To determine if rNFH-SA could be assembled into a protein brush, the immobilization of the protein on maleimide-functionalized substrates was monitored (see FIG. 4) using quartz crystal microbalance with dissipation (QCM-D). The adsorption of rNFH-SA was registered as a decrease in the normalized frequency ($\Delta f/n$) and an increase in the dissipation ($\Delta D$). Using a protein concentration of ~0.5 mg ml$^{-1}$, the transition of the bound protein layer from a collapsed 'mushroom' to an extended 'brush' configuration was obtained (FIG. 5a,b). The marked change in $\Delta f/n$ and $\Delta D$ (FIG. 5a) within the first 5-10 minutes indicates rapid immobilization of the protein on the surface. After ~20 minutes, the change in $\Delta f/n$ and $\Delta D$ was much slower, suggesting that the chains initially grafted to the surface were hindering additional protein molecules from tethering. After considerable time had elapsed (~100 minutes), $\Delta f/n$ decreased further, accompanied by an increase in $\Delta D$. This observation suggests that the bound protein molecules had swollen into an extended conformation, thereby allowing access to new binding sites on the surface and accelerating the tethering of additional protein molecules. This mushroom-to-brush transition is also evident from the plot of $\Delta D$ vs. $-\Delta f/n$ (FIG. 5b), which shows that the increase in the protein-grafting rate is accompanied by a change in the structure of the surface layer. In the brush regime, each newly immobilized protein chain causes a comparatively greater increase in dissipation (observed as an increase in slope of the plot), as would be expected for an extended molecule. To achieve maximum surface coverage, the substrate was incubated with a highly concentrated protein solution (~5 mg ml$^{-1}$) for ~20 hours. The time-dependent change in $\Delta f/n$ and $\Delta D$ was monitored and the hydrated adsorbed mass per unit area was calculated (37.4 ng mm$^{-2}$) by fitting the data to the Voigt-Voinova viscoelastic layer model (FIG. 6). To obtain a true measure of the surface density without the confounding effects of brush hydration and swelling, spectroscopic ellipsometry measurements were performed on a dry surface prepared under conditions identical to the latter QCM-D measurements. The calculated surface density of 0.02 molecules nm$^{-2}$ corresponds to an intermolecular spacing of 7.75 nm (assuming a hexagonal close packing arrangement) and indicates that protein brush layers were formed. These conditions were used to generate protein-tethered surfaces for all subsequent studies, and the ellipsometric grafting density was used in subsequent analyses.

Figure 7A:
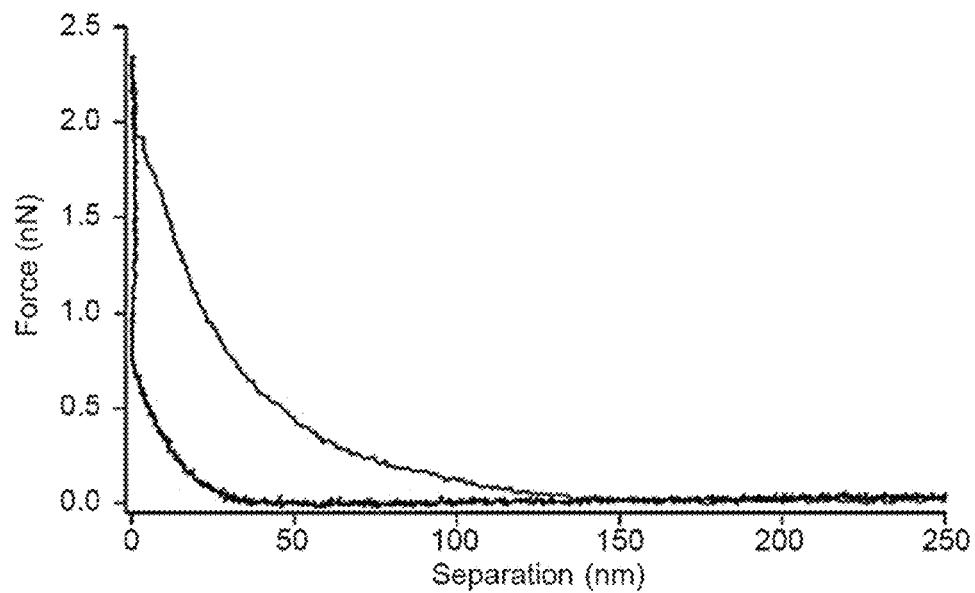
FIG. 7A-B shows comparison of force curves. AFM force-distance curves measured with either rNFH-SA or Cys immobilized on the maleimide-functionalized glass surface at (a) pH 10.9, 2 mM ionic strength and (b) pH 2.4, 4 mM ionic strength. The conditions represented here show maximum brush heights. Long-range forces are observed only in the case of protein-tethered surfaces.
Figure 7B:
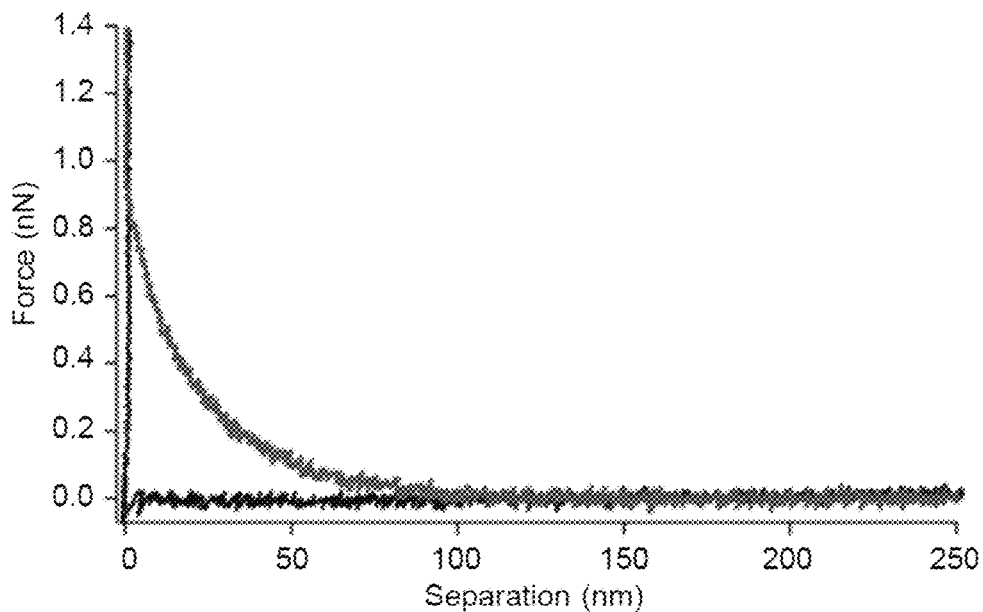
Figure 8:
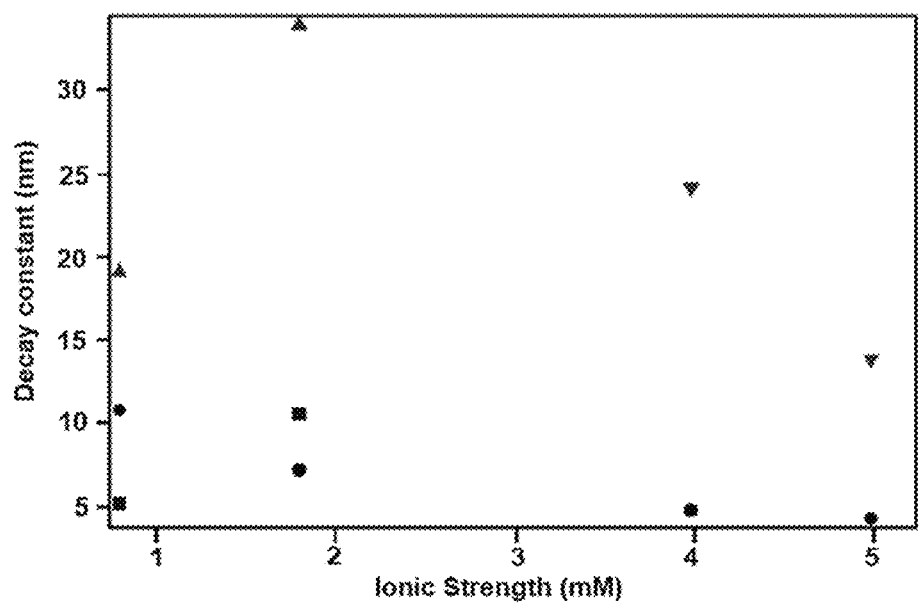
FIG. 8 shows the effect of ionic strength on Debye length and repulsive distances. Comparison between Debye length and decay constants of force profiles on Cys layer and the protein brush is shown. Sample force vs. distance (F vs. x) profiles were fitted to an exponential decay function $F=F0 \exp(-x/D)$, and the extracted decay constant (D) is plotted against total ionic strength in solution for pH 10.9 (□) and pH 2.4 (□). The force measured on protein layers is significantly more long-range than the electrostatic double-layer force that decays according to the Debye length, thereby validating the presence of an extended brush layer on the surface.

To further quantify and characterize the bound layer of rNFH-SA, atomic force microscopy (AFM) was used to measure forces exerted by the immobilized IDP layer (FIG. 7). The experiments were performed at pH 2.4 and 10.9 to encompass the nominal pK$_a$ values of glutamate and lysine, and render rNFH-SA highly positively or negatively charged respectively. Strong tip-sample repulsive forces were observed from rNFH-SA layers at separation distances much greater than the Debye length (FIG. 8). The long-range repulsive forces measured on rNFH-SA surfaces, in comparison to Cys-immobilized surfaces (FIG. 7), indicate the presence of a brush layer and are consistent with the QCM-D data.

Figure 9A:
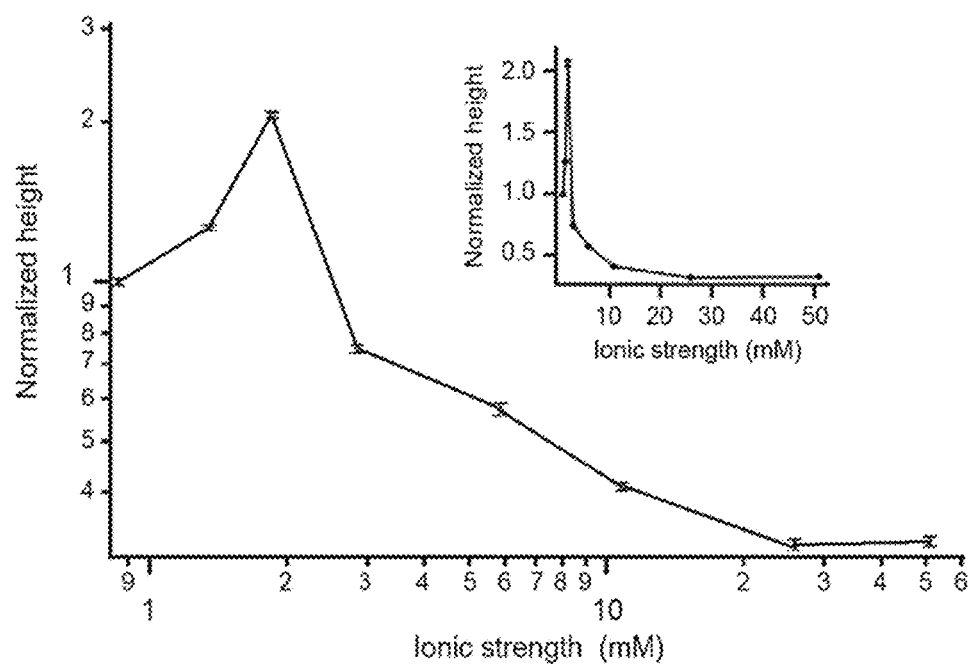
FIG. 9A-B shows changes in brush height as a function of ionic strength. Brush heights were measured at (a) pH 10.9 and (b) pH 2.4. To account for potential sample-to-sample variations, data values are normalized to the brush height measured at pH 10.9, 0 mM NaCl for the corresponding surface (57±4 nm). The insets depict the same data plotted on linear scales. Error bars indicate s.e. of the normalized brush height calculated for 400-800 force curves sampled at different points on the surface.
Figure 9B:
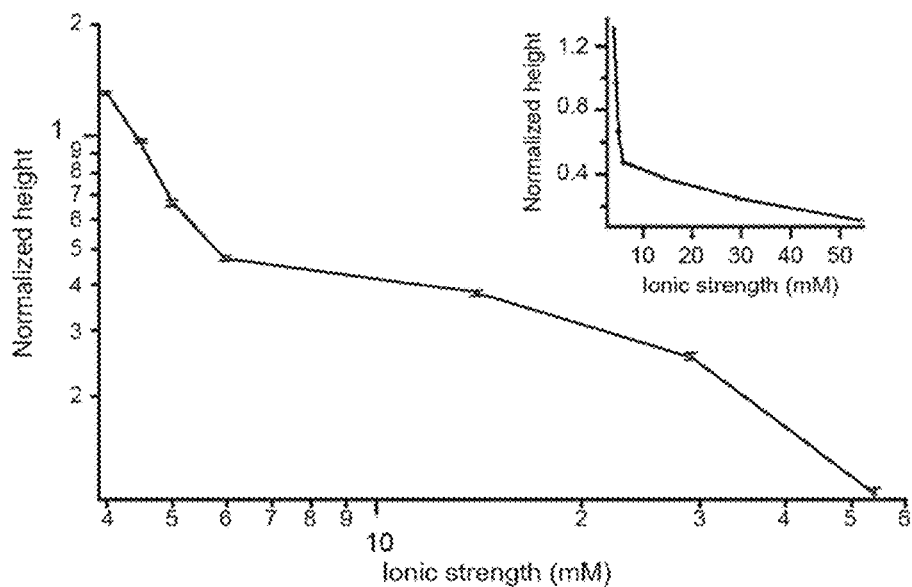
Figure 10A:
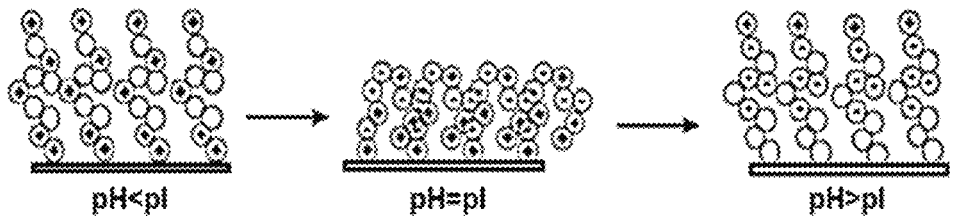
FIG. 10A-B shows a simplified scheme depicting the variation in brush height. a, pH dependence. b, ionic strength dependence. The dots represent the cations and the anions provided by the salt that are trapped within the brush.
Figure 10B:
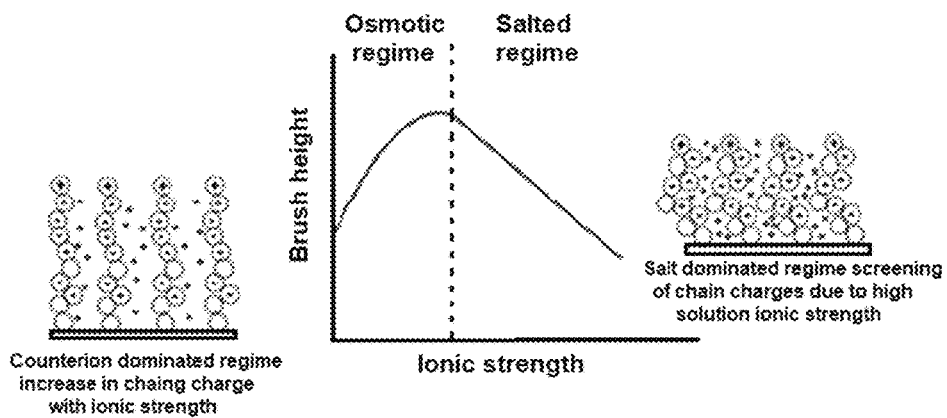

Influence of Ionic Strength on the Brush Height. To explore the properties of the IDP brush, AFM measurements were repeated over a range of ionic strengths (I) and the brush height was estimated as the tip-sample separation at which the force began to increase from zero (FIG. 9). At both pH values, a regime in which brush height decreased with increasing ionic strength (I>2 mM for pH 10.9; the entire range for pH 2.4) was observed. These observations can be rationalized based on polyelectrolyte theory since the IDP behaves like a highly charged polymer under the chosen pH conditions. At I>2 mM, the protein brush is forced into the 'salted brush' regime due to the imbalance in the ionic strength inside and outside the brush. As the ionic strength increases, the charges on the chains are progressively screened leading to a reduction in electrostatic repulsion and a decrease in brush height (FIG. 10). The experimental results (FIG. 9) show a qualitative agreement with the mean-field theory of weak polyelectrolyte brushes (FIG. 11), which predicts that the brush should collapse with increasing salt concentration (C), but only as a relatively weak power law (C$^{-1/3}$). A comparatively steeper ionic strength-dependence, which has been previously observed in synthetic polymer systems, was seen and may arise from the local modulation of protein charge-based interactions due to added salt.

Figure 11:
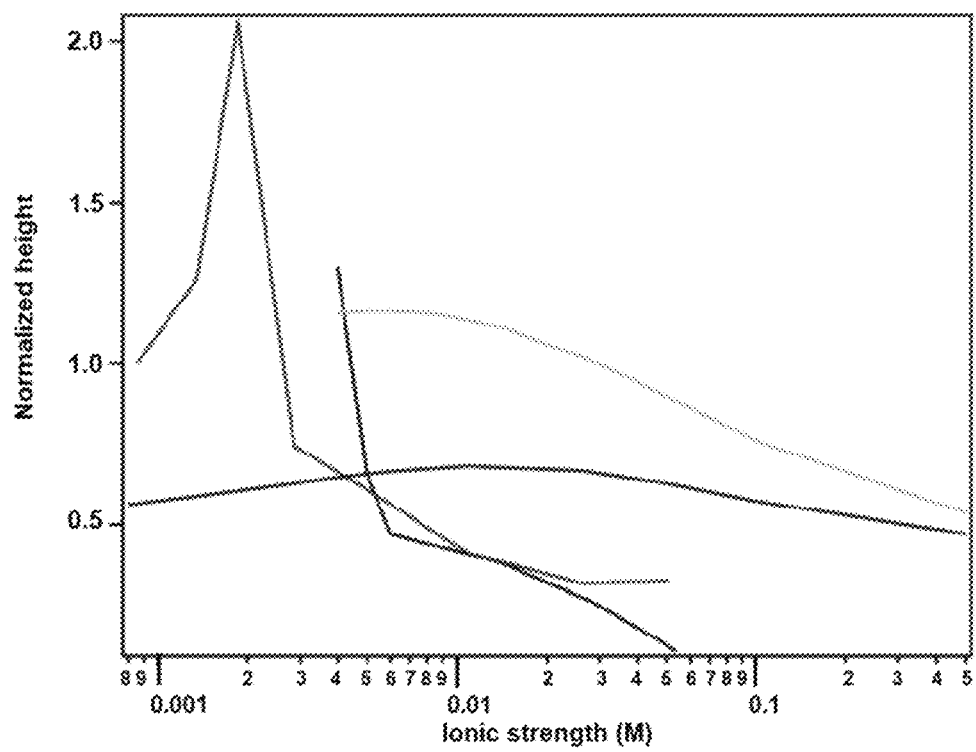
FIG. 11 shows theoretical dependence of brush height on ionic strength. Predicted ionic strength dependence of the brush height calculated based on mean-field theory, at pH values of 10.9 and 2.4 is shown. The crossover concentration is predicted to be 6.0 mM at pH 2.4 and 10.8 mM at pH 10.9. The experimental data at pH 10.9 and pH 2.4 is shown.

At pH 10.9, below a critical ionic strength (~2 mM), the system enters an 'osmotic brush' regime in which the brush height increases with ionic strength. This phenomenon is based on a shift in the protonation/deprotonation equilibrium at low ionic strengths. The local concentration of protons within the brush in the absence of salt is governed by the requirement of charge neutrality. However, when a small amount of salt is added, some of these cations can be exchanged with the protons inside the brush without affecting charge neutrality. As a consequence, the pH within the brush increases, thereby increasing the degree of deprotonation of the protein chains. This results in greater chain stretching due to counterion-induced osmotic swelling and increased inter- and intra-molecular electrostatic repulsion associated with chain ionization, as has been observed with synthetic polyelectrolyte and polyampholyte brush systems. Above a critical ionic strength, this exchange mechanism saturates and the system enters the 'salted brush' regime, in which further addition of salt collapses the brush due to electrostatic screening (FIG. 10 and FIG. 11). An analogous low-salt 'osmotic brush' regime was not observed at pH 2.4 due to the high baseline ionic strength.

Figure 12:
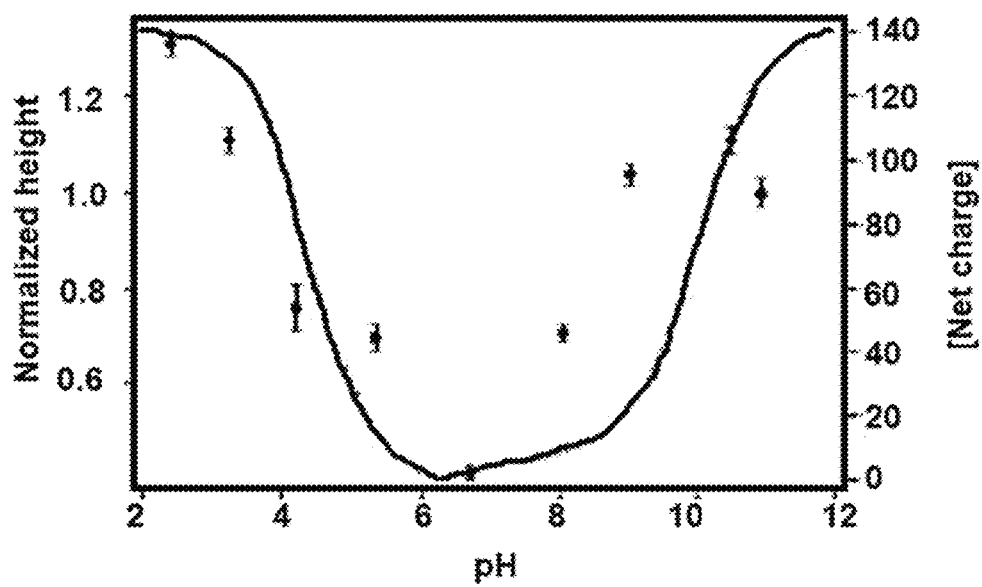
FIG. 12 shows variations in brush height as a function of pH. Variations in brush height as a function of pH. Brush heights (closed circle) were measured with no additional salt added to the solution. All brush heights have been normalized to the value at pH 10.9, 0 mM NaCl. The predicted absolute value of the charge on the protein (assuming free amino acid pKa values and irrespective of the nature of charge) is shown as a broken line for comparison. Error bars indicate s.e. of the normalized brush height calculated for 400-800 force curves sampled at different points on the surface.
Figure 13:
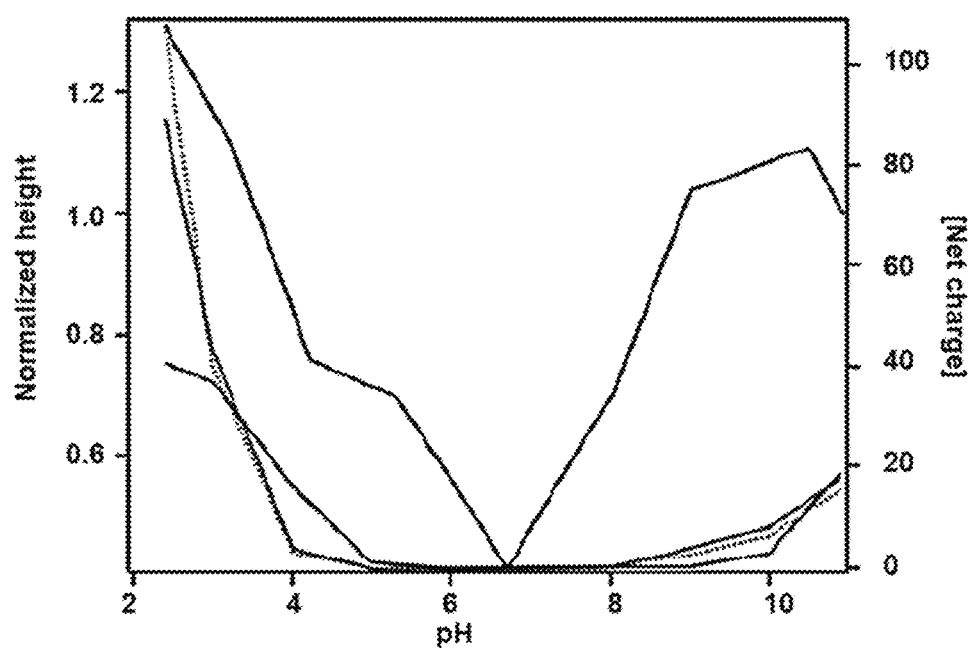
FIG. 13 a theoretical dependence of brush height on pH. Predicted pH dependence of brush heights calculated based on mean-field theory as a function of pH at 0 M and 0.1 M bulk salt concentrations is shown. The observed trend is largely explained by the variation of net protein charge Q with pH (shown for 0 M salt as a dotted line). The experimental data, which was obtained with no added salt, is shown for comparison.

Influence of pH on the Brush Height. The possibility of pH-induced conformational changes were analyzed in the rNFH-SA brushes (FIG. 12). A range of pH values was chosen that encompassed the nominal pK$_a$ of glutamate (4.1), the theoretical pI of the protein (6.3), and the nominal pK$_a$ of lysine (10.7). At pH>10.7, the carboxylate sidechains are charged, while the lysine sidechains remain largely neutral. Here, polyelectrolyte effects dominate. As the pH is decreased, the lysine sidechains are protonated, increasing the number of cationic residues along the polymer chain. Polyampholyte behavior now dominates, with salt bridges forming between oppositely charged sidechains along the length of the protein (or between protein chains in close proximity) resulting in a collapsed brush conformation. This behavior continues through the minimum of the curve until the pI is reached. As the pH is reduced further, the carboxylate sidechains become progressively protonated and thus neutral; simultaneously, the lysine sidechains gain additional cationic character, and polyelectrolyte behavior is again observed (FIG. 10). The expansion observed at the extremes are likely due to repulsive interactions between closely spaced like-charges. These effects collectively produce a threefold variation in brush thickness over this pH range. Such pH-responsive thickness changes were recently reported in more modest form (1.2-1.6 fold) for immobilized resilin-mimetic protein bilayers. When the magnitude of the charge on the protein at various pH values is compared with the pH dependence of brush height, both curves follow a similar trend, attaining maxima of charge and height at either end of the pH spectrum. Interestingly, there is a slight pH offset between the two curves, which may be due to the fact that the theoretical charge curve assumes the nominal pK$_a$ values of the free amino acids. Comparison of the observed pH dependence with calculations based on the mean-field theory (FIG. 13) suggests that the local chemical and electrostatic environment in the brush produces pK$_a$ shifts in some or all of the titratable residues. This pI-centered swelling behavior was observed for synthetic polyampholytes with charges randomly distributed along their length, which displayed at least threefold higher degree of swelling than mixed brushes of oppositely charged polyelectrolytes. Recombinantly redistributing local charge density within rNFH-SA offers additional opportunities to expand and tune these swelling dynamics.

Figure 14A:
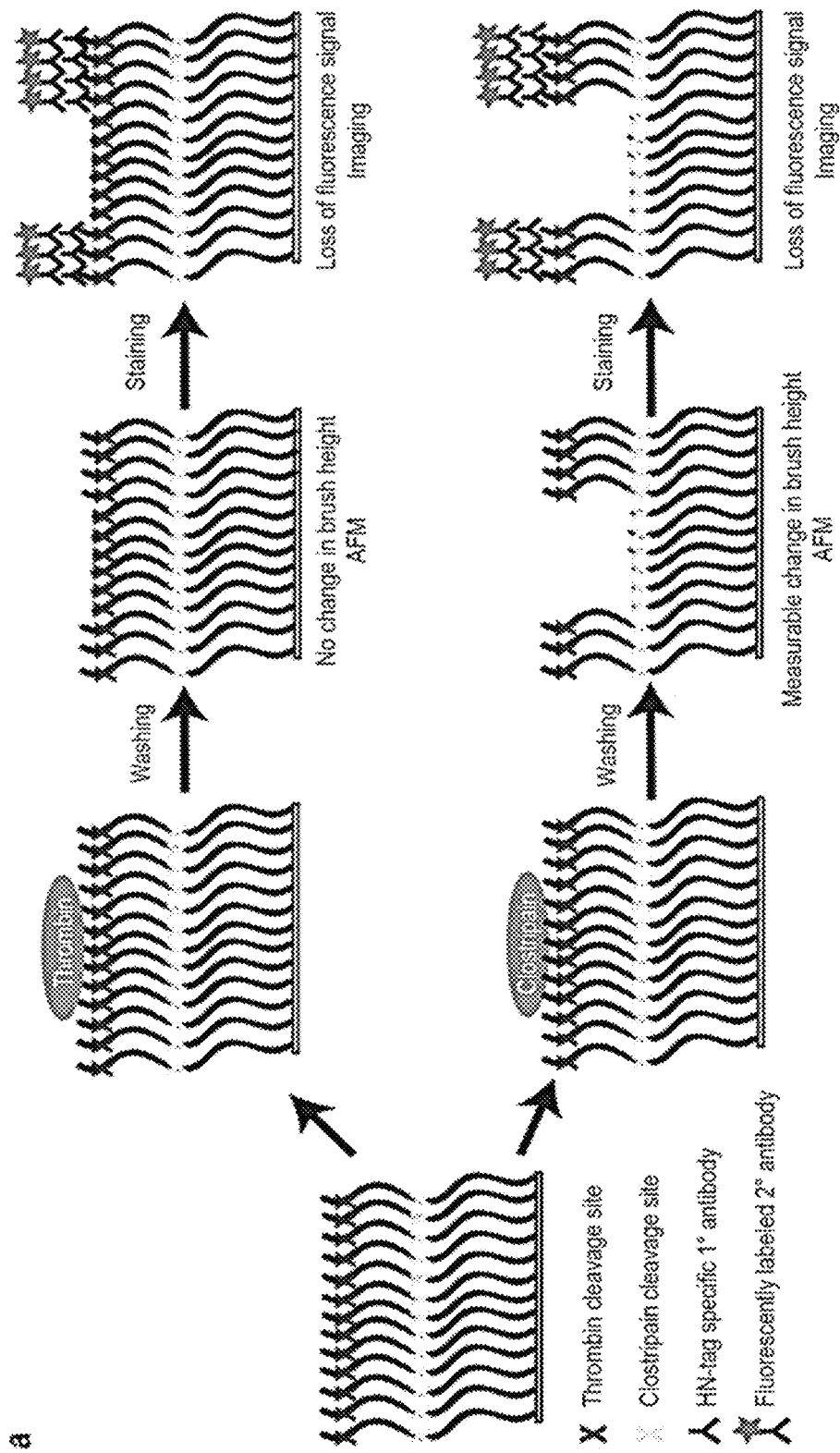

In Situ Protease Digestion of rNFH-SA Brushes. An additional and relatively unique feature of a protein-based brush is the ability to incorporate proteolytic cleavage sites into the polymer chain, which enable shortening or "shaving" of the protein brush with high precision upon addition of the cognate protease. To explore this concept, rNFH-SA brushes were assembled and one of two proteases were applied: thrombin, a serine protease that cleaves rNFH-SA at a recognition site (LVPR|GS) located just ahead of the HN-tag on the C-terminus of the protein, and clostripain, an ArgC endoproteinase that cleaves at five sites along the length of the protein, the deepest of which is 253 residues from the top edge of the brush (FIG. 14a). A droplet of the protease was incubated with the rNFH-SA brush for a defined time before being washed off, and then the C-terminal HN-tag was visualized by immunofluorescence (FIGS. 14b and 14c). Both enzymes are capable of cleaving off the HN-tag as evidenced by the loss of fluorescence in the region exposed to the protease; furthermore, enzymatic cleavage was reasonably well-confined within the droplet boundary, effectively patterning the brush height via confined proteolysis. By treating with the appropriate enzyme and measuring resulting changes in brush height by AFM, one can specifically and spatially "shave" the brush at the expected sites along the sequence (FIGS. 14d and 14e). Specifically, addition of thrombin produced a loss of fluorescence (indicating successful enzymatic cleavage) without producing a significant change in brush height by AFM. Conversely, addition of clostripain produced the same loss of fluorescence while reducing brush height by 20%. Thus, brush height may be modulated in situ under physiological conditions to precise and predictable values by taking advantage of proteolytic cleavage sites, which in principle could be designed into the sequence a priori.

The disclosure provides a protein-based polymer brush system whose conformational properties can be strongly modulated by changes in pH and ionic strength. Notably, this material is recombinantly expressed, forms brushes, and yields a nearly six- to tenfold dynamic range in brush thickness as ionic strength is varied and a threefold range as pH is varied. This dynamic range is comparable to many existing synthetic polymer brush systems, thus providing an attractive complement or alternative to synthetic systems in specific settings. In addition, the dynamic range can be shifted, widened, or narrowed in interesting ways by exerting more control over the grafting density, such as by using cloud point grafting to achieve very dense brushes. Furthermore, proteases can be used to reduce the height of the brush in situ by cleaving the constituent chains at well-defined points. The extensive suite of proteases and protease recognition sites—any of which could be introduced into the sequence at one or more arbitrary positions—provides a versatile toolbox for controlling IDP brush properties in a dynamic and specific manner. Analogous enzymatically addressable materials have been explored for a variety of applications such as payload delivery, diagnostic monitoring and ligand presentation.

Although much effort has focused on understanding the biological function of endogenous IDPs, the disclosure demonstrates that proteins represent an untapped resource for biomaterial design. IDPs could contribute to the development of new biosynthetic coatings, fusion proteins whose functions may be sterically gated, and novel cell surface engineering strategies. As described. earlier, IDPs may be designed. de novo, synthesized at high purity, and chemically tailored at specific positions along the chain through mutagenesis. IDP sequences can be optimized. for specific applications through. directed-evolution approaches and synthesized to include bio-orthogonal chemical moieties via the use of unnatural amino acids. Indeed, IDPs based on nucleoporin proteins have recently been incorporated into synthetic gated pores and surface-grafted layers, supporting the idea that IDPs can be manipulated in ways that are analogous to synthetic polymers. Together with these efforts, our work hints at the value of exploring IDPs as a new class of "smart" biomaterial building blocks.

Example 2

Materials. Fluorescein-labeled, as well as unlabeled polyethylene glycol derivatives were purchased from Nanocs, 5-((2-(and-3)-S-(acetylmercapto) succinoyl) amino) Fluorescein (SAMSA fluorescein) from Thermo Fisher Scientific and tri(ethylene glycol)-undecanethiol from Dojindo Molecular Technologies. All other chemicals were purchased from Sigma Aldrich. Quartz chips for Quartz Crystal Microbalance were purchased from Biolin Scientific, and gold substrates for Surface Plasmon Resonance were purchased from XanTec Bioanalytics.

Peptide synthesis and purification. The peptides were synthesized on solid phase using standard fluorenylmethyloxycarbonyl (FMOC)-based chemistry, cleaved from the resin, and purified by HPLC. All peptides were cleaved from resin with a cocktail of 95% trifluoroacetic acid (TFA), 2.5% H2O and 2.5% triisopropylsilane for 2 hrs, and precipitated in cold diethyl ether. After evaporating the TFA, crude peptides were purified using semi-preparative reversed-phase HPLC and subsequently lyophilized before use. HPLC was performed on an Agilent 1100 series HPLC system (Agilent Technologies, USA). Sample analysis for all HPLC experiments was achieved with an in-line diode array detector (DAD) and an in-line fluorescence detector (FLD). Semi-preparative HPLC was performed using a C18 Gemini 5 µm 110 Å reverse-phase column (250 mm×10 mm) (Phenomenex, USA). A MeCN/ddH2O gradient containing 0.1% TFA at a flow rate of 3.0 mL/min was used as the mobile phase. Matrix assisted laser desorption-ionization time of flight (MALDI-TOF) mass spectra were obtained on Voyager DE-PRO (Applied Biosystems, USA). R-cyano-4-hydroxycinnamic acid (CHCA) in 3:2 MeCN/$H_2O$ (0.1% TFA) was used as the matrix. 5(6)-carboxyfluorescein was used to fluorescently label the N-termini of peptides. The final FMOC deprotection was performed on 25 mg resin in 20% v/v 4-methyl piperidine in dimethylformamide (DMF) for 30 min at room temperature. After the resin was rinsed with DMF, 1 mL solution of 0.4 M 1-Hydroxybenzotriazole hydrate (HOBt) and 0.4 M carboxyfluorescein in DMF was added. The amide coupling reaction was then initiated by the addition of 140 µL of 50% v/v N,N'-Diisopropylcarbodiimide (DIC) in DMF and incubated at room temperature for 2 hours with gentle agitation. The resin was rinsed with DMF, MeOH, dichloromethane, and then dried under vacuum. The fluorescently labeled peptides were then cleaved from the resin and purified with HPLC.

Small angle x-ray scattering (SAXS). SAXS measurements were conducted using the SIBYLS beamline at the Advanced Light Source facility of the Lawrence Berkeley National Laboratory. Peptides at a concentration of 1 mg/ml in HEPES buffers of different ionic strengths were analyzed over a scattering vector (q) range of 0.03-0.3/Å with an exposure time of 1 second in triplicate. Similar measurements were also carried out for the different buffer preparations (blank measurements) and the resultant spectra were subtracted from the experimental peptide spectra to obtain the final data. Guinier plots were used to verify that the peptides did not aggregate. The SAXS spectra were then subjected to ensemble-optimized modeling using the ATSAS software package ([http://www.]embl-hamburg.de/biosaxs/eom.html). This analysis is based on the generation of a large pool of theoretical structures (typically 10,000) based on side-chain interaction constraints from the primary sequence of the peptides. The theoretical X-ray scattering profiles calculated from these structures are then matched for fit with the experimental scattering profile to create an ensemble of best-fit structures.

Surface plasmon resonance (SPR) measurements. All SPR measurements were performed at 25° C. in a four flow cell Biacore 3000 instrument (GE Healthcare) on bare gold SPR transducers. KDP peptide and KSP peptides were immobilized on flow channels 1 and 2 respectively via their N-terminal cysteine residues. Tri(ethylene glycol)-undecanethiol, which forms a reference layer was immobilized on flow channel 3. Immobilization was carried out by injecting 1 mM of the appropriate molecule in HEPES buffer (HBS, pH 7.5, ionic strength 150 mM) into the channels for 40 minutes at a flow rate of 5 µl/min. All flow channels were subsequently rinsed with the buffer for 30 minutes to remove any non-specifically adsorbed material. Following this, injections of BSA in HEPES buffers of various ionic strengths and pH were carried out to measure the heights of the surface layers. Prior to the BSA injections, all flow channels were equilibrated with the appropriate buffer for 15 minutes. 3 injections of BSA (each lasting 1 minute, followed by a rinse for 1 minute) at a concentration of 1 mg/ml in the corresponding buffer was carried out into all flow channels at a rate of 10 µL/min, with each injection passing all flow channels sequentially. Average response units for each BSA injection was measured relative to the buffer baseline.

Analysis of SPR data. Immobilization densities (☐) of the peptides was calculated from the change in the resonance units (ΔRU) by using the relationship 1300 RU=1 ng/mm². The grafting distance (g) could then be calculated from the density using the relationship $$g(nm) = \sqrt{\frac{M_w \cdot 10^{21}}{N_A \cdot \rho}} \quad (5)$$

where $M_w$ is the molecular weight of peptide and $N_A$ is Avogadro's number.

Heights of the layers were calculated from the response of the BSA injections by using the relation:

$$H_B = \frac{l_d}{2} \ln\left(\frac{R_{RL}}{R_B}\right) + H_{RL} \quad (6)$$

where $H_B$ and $H_{RL}$ are the heights of the peptide brush and the reference layer (2 nm) respectively, $R_B$ and $R_{RL}$ are the SPR signals during the injection of BSA on the brush and reference layer respectively, and $l_d$ is the decay length of the surface plasmon. Calculation of optimal $l_d$ for each layer under the various buffer conditions was carried out using the iterative procedure. Modeling of the SPR reflectivity spectrum necessary for the evaluation was done via Fresnel equations using a transfer matrix formalism.

Quartz Crystal Microbalance with Dissipation. QCM-D measurements were performed with a Q-Sense E4 system (Biolin Scientific). Quartz crystals with fundamental frequencies of ~5 MHz were functionalized with maleimide moieties as described below and used for immobilization of the peptides. 1 mM of the peptides in HBS were injected into the flow cell at a flow rate of 100 µl/min for 2 minutes, using a syringe pump. Change in frequency (Δf) and dissipation (ΔD) were measured at 5 overtones (n=3, 5 . . . 11) simultaneously. The data were fit using the Voight-Voinova model for viscoelastic films to obtain the surface density of the hydrated peptide layer bound to the surface.

Functionalization of Silica and Quartz Surfaces. Substrates were activated via plasma cleaning prior to functionalization. After rinsing with water and drying in a nitrogen stream, the surfaces were subsequently silanized with glycidyloxypropyltrimethoxysilane for 45 minutes at 75° C. The surfaces were then rinsed with acetone and reacted with diaminopropane for 4 hours at 75° C. After rinsing with water and drying in a nitrogen stream, the surface amines were reacted with a saturated solution of 3-(Maleimido) propionic acid N-hydroxysuccinimide ester in dry dimethylformamide (DMF) for 45 minutes at room-temperature to yield maleimide-functionalized surfaces. Functionalization of SAIM substrates with KDP and KSP peptides was carried out by incubating the maleimide-functionalized substrates with a solution of 100 µM fluorescein-labeled peptide and 1 mM unlabeled peptide in HEPES buffered saline (HBS, 150 mM NaCl, pH 7.5) for 30 minutes at room temperature. Functionalization with PEG was similarly carried out by reacting the maleimide-functionalized substrates with a solution of 100 µM fluorescein-labeled PEG and 1 mM unlabeled PEG in HBS. For functionalization with fluorescein, the maleimide-functionalized SAIM substrates were incubated with a solution containing 100 µM activated SAMSA-fluorescein (Thermo Fisher Scientific) and 1 mM acetic acid in HBS.

Scanning angle interference microscopy (SAIM) imaging. N-type [100]-orientation silicon wafers with 1933 nm silicon oxide (Addison Engineering) were cut into ~0.5 cm² chips using a diamond pen. The substrates were functionalized with the peptides, PEG and fluorescein as described was used. SAIM calibration wafers were prepared by sonicating carboxylate-modified red fluorescent spheres (100 nm; Invitrogen), following by bead deposition (5×10⁸ beads per mL) in PBS. Imaging was performed on an inverted Ti-E Perfect Focus System (Nikon) controlled by Metamorph software, equipped with 488 nm, 561 nm, and 640 nm lasers, a motorized laser Ti-TIRF-E unit, a 1.49 NA 100×TIRF objective, an electron-multiplying charged-coupled device (emCCD) camera (QuantEM 512; Photometrics), and with a linear glass polarizing filter (Edmunds Optics) in the excitation laser path. Imaging and analysis was performed.

As described solid-phase peptide synthesis was used to generate two 32-residue peptides based on the NF-H sidearm domain. The first peptide contained four KSP motifs (KSP peptide), while in the second the serine residues were replaced with aspartate residues (KDP peptide) (FIG. 15A). Comparison of the KSP and KDP peptides is expected to yield insight into electrostatic effects associated with changes in chain charge on IDP structure and stimulus-responsiveness. Additionally, as aspartate residues are sometimes used to mimic effects of phosphorylation in proteins, this approach may also lend insight into how serine phosphorylation in these sidearm domains contributes to NF structure and interactions in the cytoskeleton.

Figure 15B:
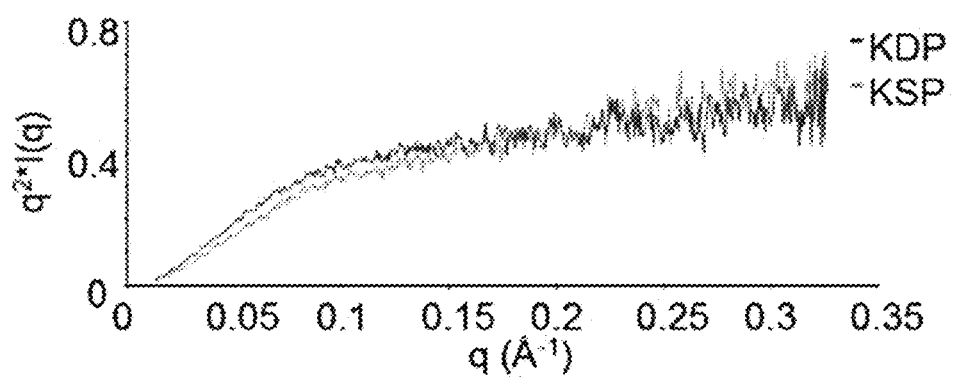

Conformational dynamics of peptides in solution. The conformational properties of each peptide in solution were characterized using small angle X-ray scattering (SAXS), which has been extensively applied to capture solution dimensions of both structured and disordered proteins and peptides. Kratky plots of the SAXS data for the two peptides in HEPES buffered saline (HBS, ionic strength 150 mM, pH 7.5) reveal a plateau at high value of the scattering vector, q, which is the signature characteristic of random coils (FIG. 15B). This confirms that these peptides lack structure, as expected. In order to extract quantitative information on peptide dimensions from the scattering data, the ensemble-optimized modeling (EOM) method was used, which has been previously established to be a more potent scheme than the traditional Guinier approach for interpreting SAXS spectra of intrinsically disordered proteins. Modeling the data in this fashion, radii of gyration (Rg) were obtained of 2.01±0.06 nm and 1.88±0.05 nm for the KDP and KSP peptides, respectively.

The lower Rg of the KSP peptide is consistent with recent molecular dynamics (MD) simulations of the C-terminal tails of the NF-H protein, which found that the non-phosphorylated sidearm domain is stabilized by salt bridges between glutamate and lysine residues; these attractive electrostatic interactions would presumably be destabilized by the electrostatic repulsions associated with added negative charge upon phosphorylation. To investigate these electrostatic effects in a more detailed manner, SAXS experiments were conducted on the peptides as a function of ionic strength. Interestingly, the dependence of Rg on ionic strength for the KSP and KDP peptides (also calculated using EOM, FIG. 15C) exhibit distinct behavior. The Rg of KDP decreases monotonically with ionic strength. This is consistent with classical polyelectrolyte theory, which would predict that salt-mediated screening of electrostatic repulsions within the peptide should induce chain condensation. The Rg of the KSP peptide, in contrast, initially falls with increasing ionic strength for ionic strength<200 mM and then rises again for ionic strength>200 mM. Aspects of these trends are predicted by the polyampholyte theory of Higgs and Joanny, which has been previously used for modeling the Rg of short intrinsically disordered proteins of approximately 50 residues in solutions of guanidium hydrochloride. According to this theory, for polyampholytes with high net charge, the Rg is expected to fall with increasing ionic strength, while for polyampholytes with medium net charge, the Rg is expected to fall up to a critical ionic strength, followed by an increase. These trends are qualitatively in tune with the observations, with the nominal net charge on KSP and KDP being −1 (medium) and −5 (high) (7 positive charges for both, and 8 and 12 negative charges for KSP and KDP respectively). Interestingly, MD simulations of the full-length sidearm domain of NF-H show that the Rg of the phosphorylated sidearm is expected to decrease with increasing ionic strength as observed. For the non-phosphorylated sidearm domain, the Rg is expected to remain constant up to an ionic strength of approximately 40 mM, followed by a small increase.

Figure 15C:
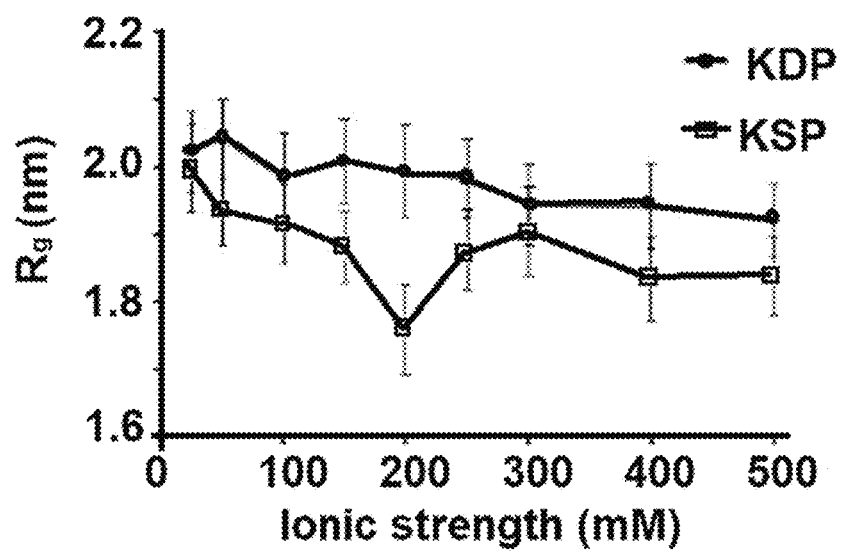
Figure 16A:
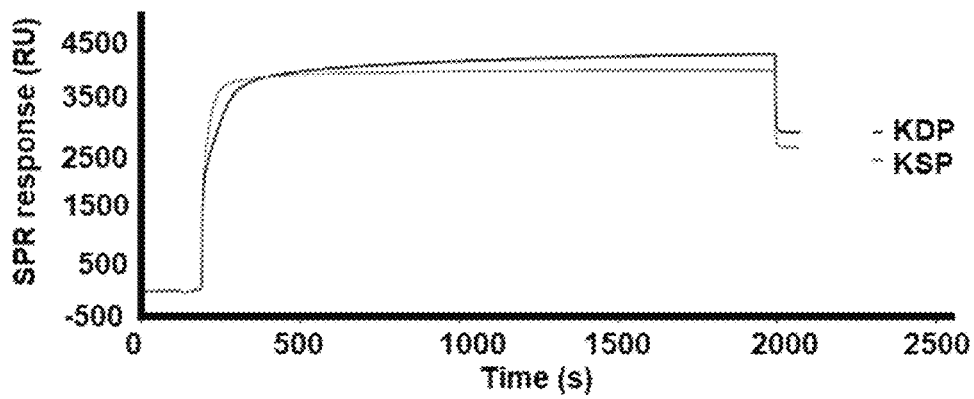
FIG. 16A-C shows (A) Representative SPR responses for the immobilization of KSP and KDP peptides on SPR transducer surfaces. (B) Representative SPR responses during the injection of BSA dissolved at a concentration of 1 mg/ml in HBS (pH 7.5, ionic strength 150 mM) on surfaces functionalized with KSP and KDP brushes, as well as on a reference layer composed of tri(ethylene glycol)-undecanethiol. The inset shows an enlarged view of the indicated region. (C) Average heights of KSP and KDP brushes at pH 7.5 and ionic strength 150 mM obtained from three separate experiments. The error bars represent standard errors calculated from the three experiments. Each experiment included three injections of BSA.
Figure 16B:
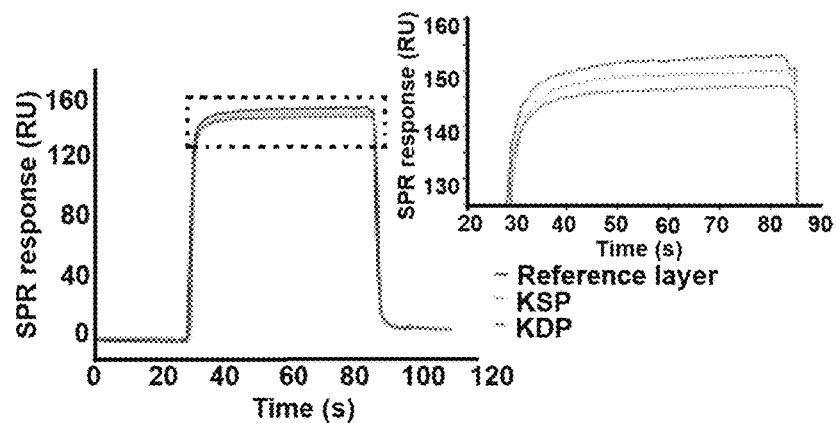
Figure 16C:
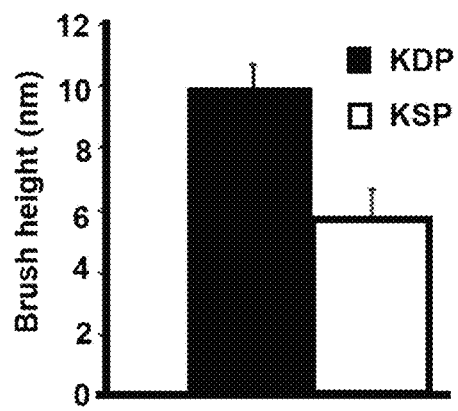

Conformational dynamics of peptide brushes. Having verified the stimulus-responsive properties of these peptides in solution, their behavior in the form of surface-anchored brushes was studied. This geometry is broadly reminiscent of the in vivo arrangement of NF-H sidearm domains within the axon, which project from the NF core to form cylindrical brushes. Moreover, as discussed earlier, the potential technological application of surface-grafted IDPs as biologically encoded interfacial materials makes this a very useful paradigm to study. KSP and KDP peptides were immobilized via their N-terminal cysteine residues on gold substrates and followed the grafting kinetics using surface plasmon resonance (SPR) (FIG. 16A). Grafting densities of 0.46 molecules/nm$^2$ and 0.5 molecules/nm$^2$ for KSP and KDP peptides, respectively, were observed. Assuming square (two-dimensional cubic) packing, this corresponds to a nearest-neighbor grafting distance of 1.47 nm for KSP and 1.41 nm for KDP. These distances are smaller than the end-to-end distances for the two peptides (4.61 nm for KSP and 4.92 nm for KDP), which can be calculated from the Rg values measured from SAXS (FIG. 15C). Based on this high surface density, the peptides form brushes on the surface. To measure the brush height, a SPR-based methodology was used as recently introduced by Schoch et al. in which bovine serum albumin (BSA) is used as a probe to measure the thicknesses of surface-grafted synthetic polymer and protein layers. In this method BSA molecules experience a steric repulsive force from the polymer/protein brush (proportional to the excluded volume of the polymer layers), which hinders their approach to the SPR transducer. The SPR response of the BSA molecules is inversely proportional to their average distance from the transducer, which enables calculation of the height of the surface-grafted brush. The SPR response of a solution of BSA in HBS (ionic strength 150 mM, pH 7.5) injected on three different surface layers (FIG. 16B) is lowest for a KDP peptide brush, higher for a KSP peptide brush and highest for a reference layer formed by tri(ethylene glycol)-undecanethiol. Analyzing these signals using the procedure described herein, a brush heights of 5.7 nm and 9.8 nm for the KSP and KDP brushes respectively (FIG. 16C).

Figure 17A:
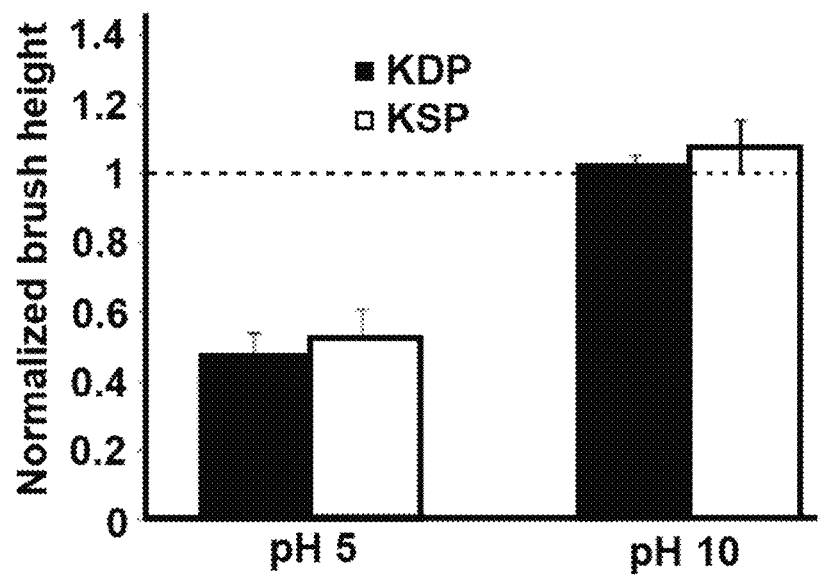
FIG. 17A-B shows (A) Heights of KSP and KDP brushes at pH 5 and 10 and ionic strength 150 mM normalized to their individual heights at pH 7.5 and ionic strength 150 mM. (B) Heights of KSP and KDP brushes at pH 7.5 and varying ionic strengths normalized to their individual heights at pH 7.5 and ionic strength 150 mM. Three experiments, each consisting of three BSA injections, were conducted, and heights were normalized for each experiment independently. The data presented are the mean and standard error of the normalized heights obtained from the three experiments.

The responsiveness of these peptide brushes was then measured with changes in pH. To do this BSA was injected in HBS of ionic strength 150 mM at different pH (pH 5 and 10), and analyzed the BSA signals following the procedure described herein. This showed that the brushes underwent significant collapse at pH 5, shrinking to around half of their previous thickness (FIG. 17A). This could be explained by the fact that the nominal charge on both peptides is lower at pH 5 than at pH 7.5 (FIG. 15A). In contrast, both brushes experienced a modest expansion at pH 10, compared to at pH 7.5 (FIG. 17A), which again correlates with the increase in the nominal charge on the peptides at pH 10 (FIG. 15A). This is consistent with the behavior of a polyelectrolyte or polyampholyte brush, where the brush height depends strongly on chain charge. Furthermore, the extreme sensitivity of the brush height close to the nominal isoelectric point (pI) of the peptide, and comparatively lesser sensitivity at distant pH values is in agreement with the previous measurements with the full-length unphosphorylated NF-sidearm domain.

Figure 17B:
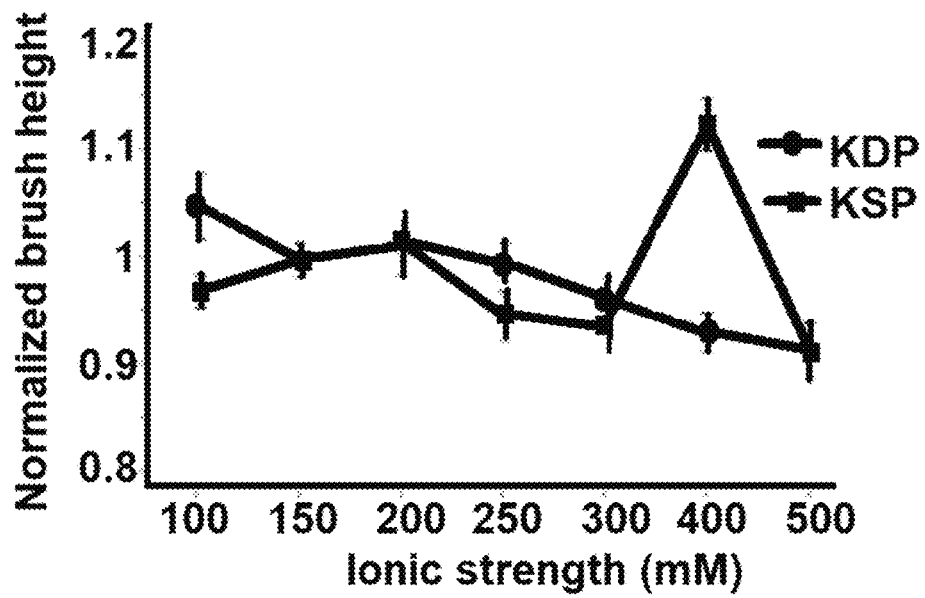

Subsequently, the responsiveness of these brushes to changes in ambient ionic strength at pH 7.5 were measured. Again, taking the approach described earlier, BSA was injected in HBS at pH 7.5 of varying ionic strengths and analyzed the SPR signal. A significant adsorption of BSA at ionic strengths below 100 mM was observed, possibly due to electrostatic attractive forces between BSA and the brushes, and so the study was confined to ionic strengths>100 mM. In the ionic strength range of 100 mM-500 mM, the brushes demonstrated very interesting and distinct responses to ionic strength (FIG. 17B). For the KDP brushes, a continuous decrease in brush height was observed with increasing ionic strength. This behavior agrees with theories developed for polyampholyte and polyelectrolyte brushes, where increasing salt concentration enhances the screening of electrostatic repulsive forces between monomers and thus produces brush collapse. This also correlates with the trend in the Rg of KDP peptide, where increasing ionic strength causes a reduction in the average polymer coil size (FIG. 15C). In contrast, the KSP peptide layer is relatively insensitive to ionic strength below 400 mM but undergoes significant expansion at 400 mM, followed by a collapse at 500 mM. While this unexpected behavior is not predicted by relevant mean field theories, the increase in height of the KSP brush at 400 mM can be hypothesized to be driven by similar mechanisms that cause the high-salt expansion of the KSP peptide at >200 mM in solution (FIG. 15C).

Figure 19:
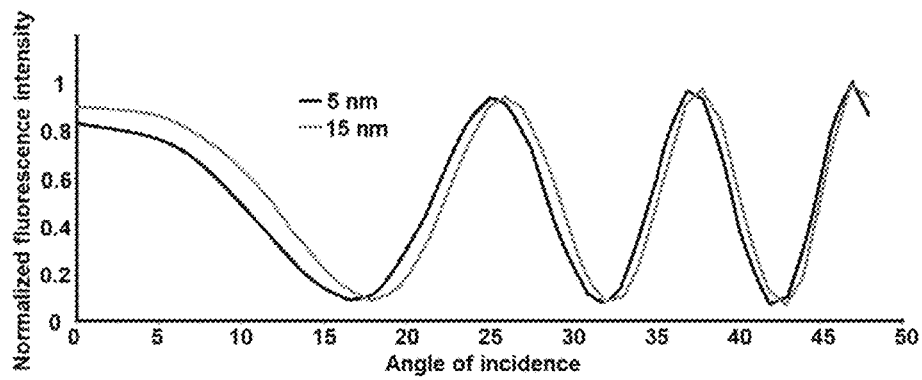
FIG. 19 shows simulated curves for variation of fluorescence intensity as a function of angle of incidence of excitation light for fluorophore-substrate separations of 5 and 15 nm.

A possible criticism of this SPR-based technique for measuring brush height is that it can be affected by adsorption of BSA to the brushes. While no significant adsorption of BSA onto peptide-functionalized surfaces were observed in the ionic strengths presented here further experiments were performed. To verify these findings with a completely independent methodology, the heights of the peptide brushes was measured using scanning angle interference microscopy (SAIM). SAIM measures the optical distance (product of physical distance and the refractive index of the intervening medium) of fluorescent species immobilized on special transducers composed of a thin film of silicon dioxide deposited on a reflective silicon wafer. The intensity of the fluorescence excitation light is axially modulated by varying the angle of incidence. Thus, the fluorescence intensity is a function of the incident angle of excitation light and the distance of the fluorophore from the silicon oxide layer (FIG. 19). This angle-dependent variation in intensity is then fit to a model to extract the height of the fluorophore above the substrate. While SAIM has been applied with great success to measure intermolecular dimensions within cellular adhesion complexes, it has not as yet been applied to reconstituted polymer brushes. Thus, the ability of SAIM to measure brush heights in a defined system in which thiol-terminated fluorescein-labeled PEG (molecular weight 5000 Da) was covalently immobilized to maleimide-functionalized SAIM substrates at high density was performed as validation. The curve for fluorescence intensity as a function of angle of incidence of excitation light for the PEG brush is shifted to the right of the curve for a comparable substrate that was functionalized with fluorescein (i.e., without the intervening PEG polymer), which confirms the higher thickness of the PEG brush (FIG. 20A). Based on this observation, heights of 6 nm and 15 nm for fluorescein- and PEG-functionalized surfaces were extracted, respectively (FIG. 20B). The height of the PEG layer could then be calculated as the difference between these two values (9 nm), which agrees with previously published heights of brushes made using PEG of this molecular weight and at comparable density.

Figure 18A:
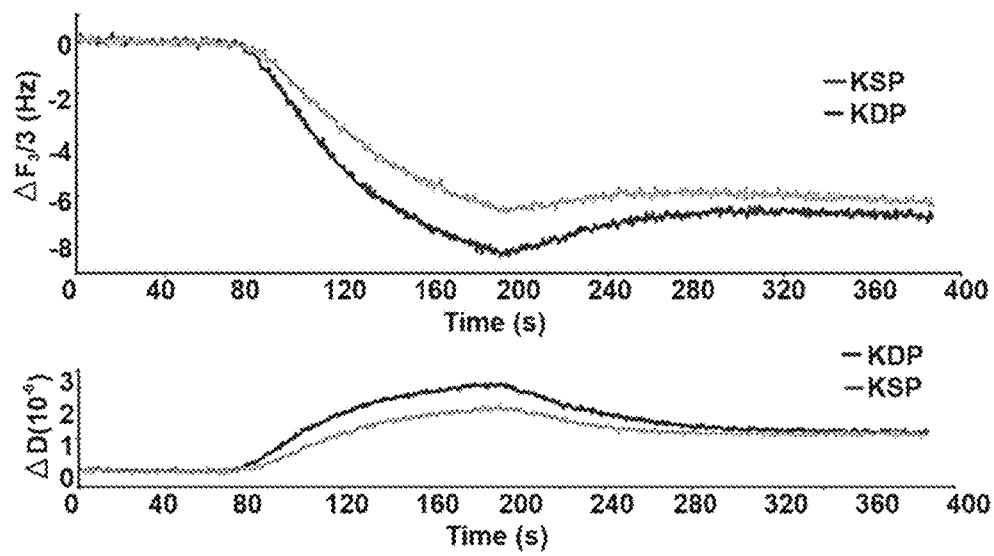
FIG. 18A-C shows (A) Change in frequency and dissipation (first overtone) signals upon immobilization of KSP and KDP peptides on substrates functionalized with maleimide groups as detected using QCM-D. (B) Heights of KSP and KDP brushes at pH 7.5 and ionic strength 150 mM measured using SAIM. (C) Heights of KSP and KDP brushes measured using SAIM at pH 7.5 and varying ionic strengths normalized to their individual heights at pH 7.5 and ionic strength 150 mM. Three experiments were conducted, and heights were normalized for each experiment independently. The data presented here are the mean and standard error of the (normalized) heights obtained from the three experiments.
Figure 18B:
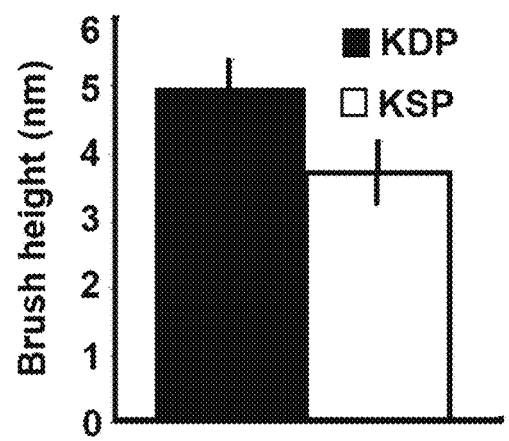

Having established SAIM as a suitable method to measure polymer brushes, the heights of KSP and KDP peptide brushes were measured using this technique. Towards this end, synthesized KSP and KDP peptides containing a cysteine on the C-terminus and labeled with fluorescein on the N-terminus were used. For SAIM studies, sequence-reversed retropeptides (PSK rather than KSP repeats; FIG. 21) were used, which facilitated the use of the N-terminus for conjugation of fluorescein on resin, and allowed immobilization via the C-terminal cysteine, while still maintaining the original order of the sequence of amino acids relative to the substrate. The immobilization of these retropeptides on quartz substrates functionalized with maleimide groups was followed with quartz crystal microbalance with dissipation monitoring (QCM-D) (FIG. 18A). A nearest neighbor grafting distance of 2.2 nm between each polymer chain using a Voigt-Voinova model to fit the QCM-D data and assuming a square packing of the peptides was determined. While this distance was greater than the grafting distance achieved in the SPR experiments, it was approximately half of the end-to-end distance of the two peptides, ensuring that the immobilized peptides adopted brush conformations. The heights of the brushes in HBS (ionic strength 150 mM, pH 7.5) was then measured using SAIM (FIG. 18B). In concurrence with the observations from the SPR-based measurements, the KSP peptide forms a thinner brush than KDP (3.7 nm and 5.0 nm for KSP and KDP respectively). The lower heights of the brushes in comparison to the SPR experiments can be explained by the lower surface density in the SAIM experiments. In addition to the different grafting densities, another possible reason for the discrepancy between the heights measured by the two techniques is that the data obtained from the SAIM measurements is modeled using a constant refractive index of the layer (1.33), which may not be strictly correct. In spite of these apparent differences in the absolute brush heights obtained from these two complementary techniques, the strong qualitative agreement between these two independent methodologies supports the notion that KDP peptides form thicker brushes than KSP peptides under comparable grafting densities and solution conditions.

Figure 18C:
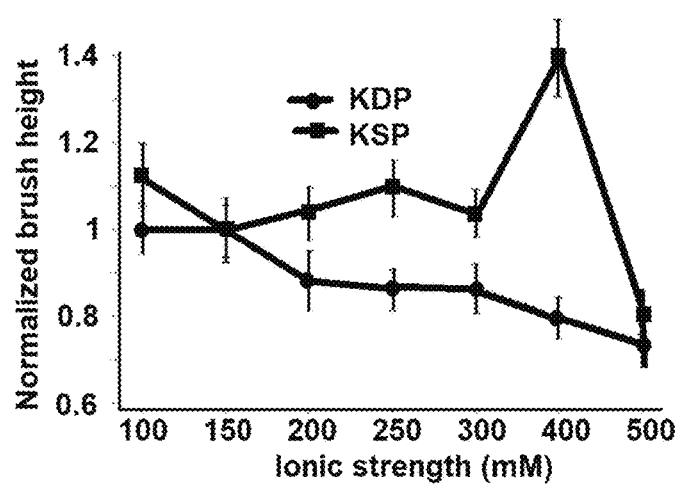

SAIM measurements were then conducted on the peptide brushes under varying ionic strengths. Again observed trends that closely follow the ones observed using the SPR experiments were identified (FIG. 18C). KDP peptide brushes displayed a monotonic decrease in brush height with ionic strength. The brush height of KSP peptides, on the other hand, was largely non-responsive to ionic strength to 400 mM followed by an abrupt increase at 400 mM, and a subsequent drop at 500 mM. Notably, the height of a surface that was functionalized only with fluorescein did not change with ionic strength, confirming that the observed brush height variations reflect the dynamics of the peptide brushes rather than any ionic strength-dependent influences on the underlying surface chemistry or fluorescein fluorescence. As with the comparison between KSP and KDP peptides in solution, these SAIM experiments confirm SPR findings that these two peptides display distinct dependences on ionic strength.

The measurements presented here are consistent with a hypothesis in which electrostatic effects associated with introduction of very few charged residues in an IDP can strongly modulate conformational and brush properties, as well as the dependence of these properties on ionic strength. These results may also have implications for how IDP phosphorylation influences conformational properties and motivates further exploration of phosphorylation (or introduction of phosphomimetic residues) as a useful design tool for engineering material properties of IDPs in solution and at solid-liquid interfaces.

Example 3

Protein-protein interactions studies utilizing the IDPs and brushes of the disclosure were also performed. Experiments using the Rho GTPase Cdc42 and its effector protein PAK1 were performed. The IDP from the soya bean (*Glycine max*) late embryogenesis abundant protein Em (Uniprot link: [http://www].uniprot.org/uniprot/I1JLC8) was used and linked to Cdc42. This IDP, which has been previously shown to act as an entropic shield, helps in preventing protein aggregation when expressed in mammalian cells. A plasmid constructs in which 1, 2 and 3 copies of Em have been recombinantly fused to the C-terminus of Cdc42 has been generated. An example of a construct is shown in FIG. 22.

A number of embodiments of the invention have been described. Nevertheless, it will be understood that various modifications may be made without departing from the spirit and scope of the invention. Accordingly, other embodiments are within the scope of the following claims.

What is claimed is:

1. A protein brush comprising:
   (a) a substrate,
   (b) a plurality of polypeptides, each polypeptide having a first end and second end, wherein the first end is linked to the substrate with an anchoring group selected from the group consisting of hydroxyl group, a thiol group, an azide group, a carboxylic acid group, an amide group, an amine group, an epoxide group, a vinyl group, peptide bond and a trichlorosilane group, wherein the polypeptides comprise a sequence of amino acids selected so as to not form secondary structure and having a desired primary sequence of charged amino acid residues so as to modulate bristle length and/or conformation, wherein the polypeptide comprises a sequence that is at least 95% identical to SEQ ID NO:3 having repeating units comprise tripeptides containing lysine and proline,
   wherein the polypeptides change conformation with the ionic and/or pH of the environment.

2. The protein brush of claim 1, wherein the polypeptide contains approximately the same number of cationic and anionic amino acids to provide a net neutrally charged polypeptide.

3. The protein brush of claim 1, wherein the polypeptide comprises at least one or more phosphorylatable amino acids selected from serine, threonine and tyrosine.

4. The protein brush of claim 3, wherein the phosphorylatable amino acids can be phosphorylated or dephosphorylated to modulate the charge on the amino acid.

5. The protein brush of claim 1, wherein the polypeptide comprises repeating sequences of charged amino acids.

6. The protein brush of claim 1, wherein the polypeptide comprises a sequence of 30 to 100 amino acids in length that is at least 90-100% identical to SEQ ID NO:1 or SEQ ID NO:2.

7. The protein brush of claim 1, wherein the polypeptide further comprises a domain selected from the group consisting of (a) a protease cleavage site, (b) a purification domain, (c) a spacer sequence, (d) a second polypeptide domain of 30 to 100 amino acids in length that is at least 90-100% identical to SEQ ID NO:1 or SEQ ID NO:2 separated by (a), (b) and/or (c).

8. The protein brush of claim 7, wherein the polypeptide comprises a protease cleavage site.

9. The protein brush of claim 1, wherein the substrate is a polypeptide of interest.

10. The protein brush of claim 9, wherein the protein brush provides a cage around the polypeptide of interest.

11. The protein brush of claim 9, wherein the polypeptide can be cleaved from the polypeptide of interest.

12. The protein brush of claim 1, wherein the substrate is a metal, metalloid, polymer, ceramic, glass or plastic.

13. A device comprising the protein brush of claim 1, wherein the device is selected from the group consisting of catheters, balloons, catheter shafts, guide wires, filters, stents, stent grafts, cerebral aneurysm filler coils, vascular grafts, myocardial plugs, patches, pacemakers and pacemaker leads, heart valves, vascular valves and tissue engineering scaffolds.

14. A method of making the protein brush of claim 11, comprising linking a coding sequence for the polypeptide of interest to a sequence encoding the plurality of polypeptides using a sequence encoding a cleavable linker to provide a construct and expressing the construct, wherein the construct produces a protein brush having a structure:
   (a) a polypeptide of interest,
   (b) a cleavable linker,
   (c) a polypeptide, wherein the polypeptide comprise a sequence of amino acids selected so as to not form secondary structure and having a desired primary sequence of charged amino acid residues so as to modulate bristle length and/or conformation, and wherein the polypeptide change conformation with the ionic and/or pH of the environment, and
   (d) an anchoring group selected from the group consisting of hydroxyl group, a thiol group, an azide group, a carboxylic acid group, an amide group, an amine group, an epoxide group, a vinyl group, peptide bond and a trichlorosilane group.

* * * * *

SEQUENCE LISTING

<160> NUMBER OF SEQ ID NOS: 6

<210> SEQ ID NO 1
<211> LENGTH: 1020
<212> TYPE: PRT
<213> ORGANISM: Homo sapiens

<400> SEQUENCE: 1

Met Met Ser Phe Gly Gly Ala Asp Ala Leu Leu Gly Ala Pro Phe Ala
1               5                   10                  15

Pro Leu His Gly Gly Gly Ser Leu His Tyr Ala Leu Ala Arg Lys Gly
            20                  25                  30

Gly Ala Gly Gly Thr Arg Ser Ala Ala Gly Ser Ser Ser Gly Phe His
        35                  40                  45

Ser Trp Thr Arg Thr Ser Val Ser Ser Val Ser Ala Ser Pro Ser Arg
    50                  55                  60

Phe Arg Gly Ala Gly Ala Ala Ser Ser Thr Asp Ser Leu Asp Thr Leu
65                  70                  75                  80

Ser Asn Gly Pro Glu Gly Cys Met Val Ala Val Ala Thr Ser Arg Ser
                85                  90                  95

Glu Lys Glu Gln Leu Gln Ala Leu Asn Asp Arg Phe Ala Gly Tyr Ile
            100                 105                 110

Asp Lys Val Arg Gln Leu Glu His Asn Arg Ser Leu Glu Gly Glu
            115                 120                 125

Ala Ala Ala Leu Arg Gln Gln Gln Ala Gly Arg Ser Ala Met Gly Glu
        130                 135                 140

Leu Tyr Glu Arg Glu Val Arg Glu Met Arg Gly Ala Val Leu Arg Leu
145                 150                 155                 160

Gly Ala Ala Arg Gly Gln Leu Arg Leu Glu Gln Glu His Leu Leu Glu
                165                 170                 175

Asp Ile Ala His Val Arg Gln Arg Leu Asp Asp Glu Ala Arg Gln Arg
            180                 185                 190

Glu Glu Ala Glu Ala Ala Ala Arg Ala Leu Ala Arg Phe Ala Gln Glu
        195                 200                 205

Ala Glu Ala Ala Arg Val Asp Leu Gln Lys Lys Ala Gln Ala Leu Gln
    210                 215                 220

Glu Glu Cys Gly Tyr Leu Arg Arg His His Gln Glu Glu Val Gly Glu
225                 230                 235                 240

Leu Leu Gly Gln Ile Gln Gly Ser Gly Ala Ala Gln Ala Gln Met Gln
                245                 250                 255

Ala Glu Thr Arg Asp Ala Leu Lys Cys Asp Val Thr Ser Ala Leu Arg
            260                 265                 270

Glu Ile Arg Ala Gln Leu Glu Gly His Ala Val Gln Ser Thr Leu Gln
        275                 280                 285

Ser Glu Glu Trp Phe Arg Val Arg Leu Asp Arg Leu Ser Glu Ala Ala
    290                 295                 300

Lys Val Asn Thr Asp Ala Met Arg Ser Ala Gln Glu Glu Ile Thr Glu
305                 310                 315                 320

Tyr Arg Arg Gln Leu Gln Ala Arg Thr Thr Glu Leu Glu Ala Leu Lys
                325                 330                 335

Ser Thr Lys Asp Ser Leu Glu Arg Gln Arg Ser Glu Leu Glu Asp Arg
            340                 345                 350

His Gln Ala Asp Ile Ala Ser Tyr Gln Glu Ala Ile Gln Gln Leu Asp
        355                 360                 365

```
Ala Glu Leu Arg Asn Thr Lys Trp Glu Met Ala Ala Gln Leu Arg Glu
370                 375                 380

Tyr Gln Asp Leu Leu Asn Val Lys Met Ala Leu Asp Ile Glu Ile Ala
385                 390                 395                 400

Ala Tyr Arg Lys Leu Leu Glu Gly Glu Cys Arg Ile Gly Phe Gly
            405                 410                 415

Pro Ile Pro Phe Ser Leu Pro Glu Gly Leu Pro Lys Ile Pro Ser Val
            420                 425                 430

Ser Thr His Ile Lys Val Lys Ser Glu Lys Ile Lys Val Val Glu
        435                 440                 445

Lys Ser Glu Lys Glu Thr Val Ile Val Glu Glu Gln Thr Glu Glu Thr
450                 455                 460

Gln Val Thr Glu Glu Val Thr Glu Glu Glu Lys Glu Ala Lys Glu
465                 470                 475                 480

Glu Glu Gly Lys Glu Glu Gly Gly Glu Glu Glu Ala Glu Gly
            485                 490                 495

Gly Glu Glu Glu Thr Lys Ser Pro Pro Ala Glu Ala Ala Ser Pro
            500                 505                 510

Glu Lys Glu Ala Lys Ser Pro Val Lys Glu Glu Ala Lys Ser Pro Ala
515                 520                 525

Glu Ala Lys Ser Pro Glu Lys Glu Glu Ala Lys Ser Pro Ala Glu Val
530                 535                 540

Lys Ser Pro Glu Lys Ala Lys Ser Pro Ala Lys Glu Glu Ala Lys Ser
545                 550                 555                 560

Pro Pro Glu Ala Lys Ser Pro Glu Lys Glu Glu Ala Lys Ser Pro Ala
            565                 570                 575

Glu Val Lys Ser Pro Glu Lys Ala Lys Ser Pro Ala Lys Glu Glu Ala
            580                 585                 590

Lys Ser Pro Ala Glu Ala Lys Ser Pro Glu Lys Ala Lys Ser Pro Val
            595                 600                 605

Lys Glu Glu Ala Lys Ser Pro Ala Glu Ala Lys Ser Pro Val Lys Glu
610                 615                 620

Glu Ala Lys Ser Pro Ala Glu Val Lys Ser Pro Glu Lys Ala Lys Ser
625                 630                 635                 640

Pro Thr Lys Glu Glu Ala Lys Ser Pro Glu Lys Ala Lys Ser Pro Glu
            645                 650                 655

Lys Glu Glu Ala Lys Ser Pro Glu Lys Ala Lys Ser Pro Val Lys Ala
            660                 665                 670

Glu Ala Lys Ser Pro Glu Lys Ala Lys Ser Pro Val Lys Ala Glu Ala
            675                 680                 685

Lys Ser Pro Glu Lys Ala Lys Ser Pro Val Lys Glu Glu Ala Lys Ser
            690                 695                 700

Pro Glu Lys Ala Lys Ser Pro Val Lys Glu Glu Ala Lys Ser Pro Glu
705                 710                 715                 720

Lys Ala Lys Ser Pro Val Lys Glu Glu Ala Lys Thr Pro Glu Lys Ala
            725                 730                 735

Lys Ser Pro Val Lys Glu Glu Ala Lys Ser Pro Glu Lys Ala Lys Ser
            740                 745                 750

Pro Glu Lys Ala Lys Thr Leu Asp Val Lys Ser Pro Glu Ala Lys Thr
            755                 760                 765

Pro Ala Lys Glu Glu Ala Arg Ser Pro Ala Asp Lys Phe Pro Glu Lys
770                 775                 780

Ala Lys Ser Pro Val Lys Glu Glu Val Lys Ser Pro Glu Lys Ala Lys
```

```
785                 790                 795                 800
Ser Pro Leu Lys Glu Asp Ala Lys Ala Pro Glu Lys Glu Ile Pro Lys
                805                 810                 815

Lys Glu Glu Val Lys Ser Pro Val Lys Glu Glu Lys Pro Gln Glu
            820                 825                 830

Val Lys Val Lys Glu Pro Pro Lys Ala Glu Glu Lys Ala Pro
            835                 840                 845

Ala Thr Pro Lys Thr Glu Glu Lys Lys Asp Ser Lys Lys Glu Glu Ala
        850                 855                 860

Pro Lys Lys Glu Ala Pro Lys Pro Lys Val Glu Glu Lys Lys Glu Pro
865                 870                 875                 880

Ala Val Glu Lys Pro Lys Glu Ser Lys Val Glu Ala Lys Lys Glu Glu
                885                 890                 895

Ala Glu Asp Lys Lys Lys Val Pro Thr Pro Glu Lys Glu Ala Pro Ala
                900                 905                 910

Lys Val Glu Val Lys Glu Asp Ala Lys Pro Lys Glu Lys Thr Glu Val
                915                 920                 925

Ala Lys Lys Glu Pro Asp Asp Ala Lys Ala Lys Glu Pro Ser Lys Pro
        930                 935                 940

Ala Glu Lys Lys Glu Ala Ala Pro Glu Lys Lys Asp Thr Lys Glu Glu
945                 950                 955                 960

Lys Ala Lys Lys Pro Glu Glu Lys Pro Lys Thr Glu Ala Lys Ala Lys
                965                 970                 975

Glu Asp Asp Lys Thr Leu Ser Lys Glu Pro Ser Lys Pro Lys Ala Glu
                980                 985                 990

Lys Ala Glu Lys Ser Ser Ser Thr Asp Gln Lys Asp Ser Lys Pro Pro
        995                 1000                1005

Glu Lys Ala Thr Glu Asp Lys Ala Ala Lys Gly Lys
        1010                1015                1020

<210> SEQ ID NO 2
<211> LENGTH: 1072
<212> TYPE: PRT
<213> ORGANISM: Rattus norvegicus

<400> SEQUENCE: 2

Met Met Ser Phe Gly Ser Ala Asp Ala Leu Leu Gly Ala Pro Phe Ala
1               5                   10                  15

Pro Leu His Gly Gly Ser Leu His Tyr Ala Leu Ser Arg Lys Ala
            20                  25                  30

Gly Ala Gly Gly Thr Arg Ser Ala Ala Gly Ser Ser Ser Gly Phe His
        35                  40                  45

Ser Trp Ala Arg Thr Ser Val Ser Ser Val Ser Ala Ser Pro Ser Arg
    50                  55                  60

Phe Arg Gly Ala Ala Ser Ser Thr Asp Ser Leu Asp Thr Leu Ser Asn
65                  70                  75                  80

Gly Pro Glu Gly Cys Val Ala Ala Val Ala Ala Arg Ser Glu Lys Glu
                85                  90                  95

Gln Leu Gln Ala Leu Asn Asp Arg Phe Ala Gly Tyr Ile Asp Lys Val
            100                 105                 110

Arg Gln Leu Glu Ala His Asn Arg Thr Leu Glu Gly Glu Ala Ala Ala
        115                 120                 125

Leu Arg Gln Gln Lys Gly Arg Ala Ala Met Gly Glu Leu Tyr Glu Arg
    130                 135                 140
```

```
Glu Val Arg Glu Met Arg Gly Ala Val Leu Arg Leu Gly Ala Ala Arg
145                 150                 155                 160

Gly His Val Arg Leu Glu Gln Glu His Leu Leu Glu Asp Ile Ala His
            165                 170                 175

Val Arg Gln Arg Leu Asp Glu Glu Ala Arg Gln Arg Glu Glu Ala Glu
                180                 185                 190

Ala Ala Ala Arg Ala Leu Ala Arg Phe Ala Gln Glu Ala Glu Ala Ala
            195                 200                 205

Arg Val Glu Leu Gln Lys Lys Ala Gln Ala Leu Gln Glu Glu Cys Gly
210                 215                 220

Tyr Leu Arg Arg His His Gln Glu Glu Val Gly Glu Leu Leu Gly Gln
225                 230                 235                 240

Ile Gln Gly Cys Gly Ala Ala Gln Ala Gln Ala Gln Ala Glu Ala Arg
                245                 250                 255

Asp Ala Leu Lys Cys Asp Val Thr Ser Ala Leu Arg Glu Ile Arg Ala
            260                 265                 270

Gln Leu Glu Gly His Thr Val Gln Ser Thr Leu Gln Ser Glu Glu Trp
            275                 280                 285

Phe Arg Val Arg Leu Asp Arg Leu Ser Glu Ala Ala Lys Val Asn Thr
290                 295                 300

Asp Ala Met Arg Ser Ala Gln Glu Glu Ile Thr Glu Tyr Arg Arg Gln
305                 310                 315                 320

Leu Gln Ala Arg Thr Thr Glu Leu Glu Ala Leu Lys Ser Thr Lys Glu
                325                 330                 335

Ser Leu Glu Arg Gln Arg Ser Glu Leu Glu Asp Arg His Gln Val Asp
            340                 345                 350

Met Ala Ser Tyr Gln Asp Ala Ile Gln Gln Leu Asp Asn Glu Leu Arg
            355                 360                 365

Asn Thr Lys Trp Glu Met Ala Ala Gln Leu Arg Glu Tyr Gln Asp Leu
370                 375                 380

Leu Asn Val Lys Met Ala Leu Asp Ile Glu Ile Ala Ala Tyr Arg Lys
385                 390                 395                 400

Leu Leu Glu Gly Glu Glu Cys Arg Ile Gly Phe Gly Pro Ser Pro Phe
                405                 410                 415

Ser Leu Thr Glu Gly Leu Pro Lys Ile Pro Ser Met Ser Thr His Ile
            420                 425                 430

Lys Val Lys Ser Glu Glu Lys Ile Lys Val Val Glu Lys Ser Glu Lys
            435                 440                 445

Glu Thr Val Ile Val Glu Glu Gln Thr Glu Glu Ile Gln Val Thr Glu
    450                 455                 460

Glu Val Thr Glu Glu Glu Asp Lys Glu Ala Gln Gly Glu Glu Glu Glu
465                 470                 475                 480

Glu Ala Glu Glu Gly Gly Glu Glu Ala Ala Thr Thr Ser Pro Pro Ala
                485                 490                 495

Glu Glu Ala Ala Ser Pro Glu Lys Glu Thr Lys Ser Pro Val Lys Glu
            500                 505                 510

Glu Ala Lys Ser Pro Ala Glu Ala Lys Ser Pro Ala Glu Ala Lys Ser
            515                 520                 525

Pro Ala Glu Ala Lys Ser Pro Ala Glu Val Lys Ser Pro Ala Glu Val
            530                 535                 540

Lys Ser Pro Ala Glu Ala Lys Ser Pro Ala Glu Ala Lys Ser Pro Ala
545                 550                 555                 560

Glu Val Lys Ser Pro Ala Thr Val Lys Ser Pro Ala Glu Ala Lys Ser
```

```
                    565                 570                 575
Pro Ala Glu Ala Lys Ser Pro Ala Glu Val Lys Ser Pro Ala Thr Val
                580                 585                 590

Lys Ser Pro Gly Glu Ala Lys Ser Pro Ala Glu Ala Lys Ser Pro Ala
                595                 600                 605

Glu Val Lys Ser Pro Val Glu Ala Lys Ser Pro Ala Glu Ala Lys Ser
            610                 615                 620

Pro Ala Ser Val Lys Ser Pro Gly Glu Ala Lys Ser Pro Ala Glu Ala
625                 630                 635                 640

Lys Ser Pro Ala Glu Val Lys Ser Pro Ala Thr Val Lys Ser Pro Val
                645                 650                 655

Glu Ala Lys Ser Pro Ala Glu Val Lys Ser Pro Val Thr Val Lys Ser
                660                 665                 670

Pro Ala Glu Ala Lys Ser Pro Val Glu Val Lys Ser Pro Ala Ser Val
                675                 680                 685

Lys Ser Pro Ser Glu Ala Lys Ser Pro Ala Gly Ala Lys Ser Pro Ala
                690                 695                 700

Glu Ala Lys Ser Pro Val Val Ala Lys Ser Pro Ala Glu Ala Lys Ser
705                 710                 715                 720

Pro Ala Glu Ala Lys Pro Pro Ala Glu Ala Lys Ser Pro Ala Glu Ala
                725                 730                 735

Lys Ser Pro Ala Glu Ala Lys Ser Pro Ala Glu Ala Lys Ser Pro Ala
                740                 745                 750

Glu Ala Lys Ser Pro Val Glu Val Lys Ser Pro Glu Lys Ala Lys Ser
                755                 760                 765

Pro Val Lys Glu Gly Ala Lys Ser Leu Ala Glu Ala Lys Ser Pro Glu
                770                 775                 780

Lys Ala Lys Ser Pro Val Lys Glu Glu Ile Lys Pro Pro Ala Glu Val
785                 790                 795                 800

Lys Ser Pro Glu Lys Ala Lys Ser Pro Met Lys Glu Glu Ala Lys Ser
                805                 810                 815

Pro Glu Lys Ala Lys Thr Leu Asp Val Lys Ser Pro Glu Ala Lys Thr
                820                 825                 830

Pro Ala Lys Glu Glu Ala Lys Arg Pro Ala Asp Ile Arg Ser Pro Glu
                835                 840                 845

Gln Val Lys Ser Pro Ala Lys Glu Ala Lys Ser Pro Glu Lys Glu
                850                 855                 860

Glu Thr Arg Thr Glu Lys Val Ala Pro Lys Lys Glu Glu Val Lys Ser
865                 870                 875                 880

Pro Val Glu Glu Val Lys Ala Lys Glu Pro Pro Lys Lys Val Glu Glu
                885                 890                 895

Glu Lys Thr Pro Ala Thr Pro Lys Thr Glu Val Lys Glu Ser Lys Lys
                900                 905                 910

Asp Glu Ala Pro Lys Glu Ala Gln Lys Pro Lys Ala Glu Glu Lys Glu
                915                 920                 925

Pro Leu Thr Glu Lys Pro Lys Asp Ser Pro Gly Glu Ala Lys Lys Glu
                930                 935                 940

Glu Ala Lys Glu Lys Lys Ala Ala Pro Glu Glu Thr Pro Ala
945                 950                 955                 960

Lys Leu Gly Val Lys Glu Glu Ala Lys Pro Lys Glu Lys Ala Glu Asp
                965                 970                 975

Ala Lys Ala Lys Glu Pro Ser Lys Pro Ser Glu Lys Glu Lys Pro Lys
                980                 985                 990
```

Lys Glu Glu Val Pro Ala Ala Pro Glu Lys Lys Asp Thr Lys Glu Glu
           995                 1000                1005

Lys Thr Thr Glu Ser Lys Lys Pro Glu Glu Lys Pro Lys Met Gln
           1010                1015                1020

Ala Lys Ala Lys Glu Glu Asp Lys Gly Leu Pro Gln Glu Pro Ser
           1025                1030                1035

Lys Pro Lys Thr Glu Lys Ala Glu Lys Ser Ser Thr Asp Gln
           1040                1045                1050

Lys Asp Ser Gln Pro Ser Glu Lys Ala Pro Glu Asp Lys Ala Ala
           1055                1060                1065

Lys Gly Asp Lys
           1070

<210> SEQ ID NO 3
<211> LENGTH: 32
<212> TYPE: PRT
<213> ORGANISM: Artificial Sequence
<220> FEATURE:
<223> OTHER INFORMATION: NF-H Fragment

<400> SEQUENCE: 3

Cys Glu Ala Lys Ser Pro Val Lys Glu Glu Ala Lys Ser Pro Ala Glu
1               5                   10                  15

Ala Lys Ser Pro Glu Lys Glu Glu Ala Lys Ser Pro Ala Glu Val Lys
                20                  25                  30

<210> SEQ ID NO 4
<211> LENGTH: 32
<212> TYPE: PRT
<213> ORGANISM: Artificial Sequence
<220> FEATURE:
<223> OTHER INFORMATION: mutant NF-H fragment

<400> SEQUENCE: 4

Cys Glu Ala Lys Asp Pro Val Lys Glu Glu Ala Lys Asp Pro Ala Glu
1               5                   10                  15

Ala Lys Asp Pro Glu Lys Glu Glu Ala Lys Asp Pro Ala Glu Val Lys
                20                  25                  30

<210> SEQ ID NO 5
<211> LENGTH: 32
<212> TYPE: PRT
<213> ORGANISM: Artificial Sequence
<220> FEATURE:
<223> OTHER INFORMATION: Reverse HF-H sequence

<400> SEQUENCE: 5

Lys Val Glu Ala Pro Ser Lys Ala Glu Glu Lys Glu Pro Ser Lys Ala
1               5                   10                  15

Glu Ala Pro Ser Lys Ala Glu Glu Lys Val Pro Ser Lys Ala Glu Cys
                20                  25                  30

<210> SEQ ID NO 6
<211> LENGTH: 32
<212> TYPE: PRT
<213> ORGANISM: Artificial Sequence
<220> FEATURE:
<223> OTHER INFORMATION: Mutant and reverse NF-H fragment

<400> SEQUENCE: 6

Lys Val Glu Ala Pro Asp Lys Ala Glu Glu Lys Glu Pro Asp Lys Ala
1               5                   10                  15

-continued

```
Glu Ala Pro Asp Lys Ala Glu Glu Lys Val Pro Asp Lys Ala Glu Cys
        20                  25                  30
```